United States Patent [19]

Shin et al.

[11] Patent Number: 6,000,284

[45] Date of Patent: *Dec. 14, 1999

[54] METHOD AND APPARATUS FOR DETERMINING AND QUANTIFYING RESISTANCE TO SCUFF DAMAGE OF A FILM ADHERED ON A PANEL

[75] Inventors: Euy-Sik Eugene Shin; Roger J. Morgan, both of Midland; Lawrence T. Drzal, Okemos, all of Mich.

[73] Assignee: Board of Trustees operating Michigan State University, East Lansing, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/832,385

[22] Filed: Apr. 2, 1997

[51] Int. Cl.⁶ ..................................................... G01N 3/56
[52] U.S. Cl. ................................................ 73/150 R; 73/7
[58] Field of Search .................................. 73/7, 9, 10, 78, 73/81, 85, 150 R

[56] References Cited

U.S. PATENT DOCUMENTS

| | | |
|---|---|---|
| 2,311,430 | 2/1943 | Beno . |
| 2,373,200 | 4/1945 | Simmons et al. . |
| 2,801,540 | 8/1957 | Rondeau . |
| 2,890,585 | 6/1959 | Albrecht . |
| 3,087,326 | 4/1963 | MacDonnell . |
| 3,123,997 | 3/1964 | Cosner ........................................ 73/81 |
| 3,289,458 | 12/1966 | Deichert et al. . |
| 3,657,921 | 4/1972 | Lang ........................................... 73/83 |
| 3,736,583 | 5/1973 | Smith et al. ................................ 73/81 |
| 3,754,436 | 8/1973 | Saxton ....................................... 73/81 |
| 3,985,026 | 10/1976 | Griffin et al. . |
| 4,791,807 | 12/1988 | Oechsle . |
| 5,438,863 | 8/1995 | Johnson . |
| 5,490,410 | 2/1996 | Markstrom . |

FOREIGN PATENT DOCUMENTS 138761  11/1960  U.S.S.R. ....................................... 73/7

OTHER PUBLICATIONS

Mitra O'Malley and Joel Kopinsky, "Automotive Environmental and Safety Rules are Key Driving Forces for Innovation," Modern Plastics Ency. 94, pp. 20–22, (Mid–Nov. 1993).

A.C. Ramamurthy, J.W. Holubka, and Dennis J. Mihora, Adhesion Mechanics During Low–Speed . . . Proceedings of the 18th Annual Mtg. pp. 52–55 (1995).

(List continued on next page.)

*Primary Examiner*—Hezron Williams
*Assistant Examiner*—Willie Morris Worth
*Attorney, Agent, or Firm*—Ian C. McLeod; Mary M. Moyne

[57] ABSTRACT

A method and system (100) for determining and quantifying the resistance to scuff damage of a film (152) adhered to a substrate (150) of a panel (154), is described. The system includes a computer (102), pressure control valves (104) and a test module (10). The test module has an indentor support plate (12) with an indentor (24 or 224), a compression moving plate (14) and an end plate (16). The plates are connected together by rods (18). The indentor support plate and the end plate are mounted at opposite ends of the rods with the compression moving plate mounted therebetween. An actuator (36) having bellows (42) is mounted between the end plate and the compression moving plate. The panel is mounted on a sliding panel support plate (58) which is connected to a load cell (106). In use, the panel support plate and the panel are positioned between the compression moving plate and the indentor support plate so that the indentor is adjacent the film on the substrate. Next, air is provided to the actuator which moves the moving plate toward the indentor support plate and causes the indentor to make contact with the film on the substrate. The panel support plate and the panel are moved down between the plates such that the indentor produces a scuff on the film. The indentation load on the panel is read by the computer from the load cell.

20 Claims, 23 Drawing Sheets

OTHER PUBLICATIONS

E.K.L. Lau et al "Mar Resistance of Polyolefins: Mechanisms, Measurements and Materials," Proc. of the Third Intl . . . Oct. 28–30 (1996) Novi, MI.

E. Eugene Shin et al "Reliability and Durability of Coated Composite Panels for Automotive Appln." Proc. of the Third Intl. Conf. & Exhibit Oct. 28–30, 1996, Novi, MI.

Michelle J. Mikulec and Thomas C. Yu, "Uppermost Stratum Morphology and Paintability of Thermo–plastic Olefins", Proc. of the Third Intl. Conf. & Exhibit, TPOs in Automotive 1996, Oct. 28–30 Novi, MI.

Rose A. Ryntz, "The Influence of Surface Morphology on the Adhesion of Coatings . . . " Proc. of the 18th Annual Meeting of The Adhesion Soc., pp. 267–273 (1995).

METHOD AND APPARATUS FOR DETERMINING AND QUANTIFYING RESISTANCE TO SCUFF DAMAGE OF A FILM ADHERED ON A PANEL

BACKGROUND OF THE INVENTION (1) Field of the Invention

The present invention relates to a method and apparatus for determining the resistance to scuff damage of a film on a panel. In particular, the present invention relates to a method and apparatus for determining and quantifying the resistance to scuff damage of paint or other films on various substrate materials including not only polymers (e.g. RIM-PU, TPO and composites) but also metals which uses an actuator to provide the correct pressure or load during testing. The actuator along with the computer controller enable the system to be repeatedly used with several different specimens or to conduct several tests on one specimen with consistent results.

The use of plastics has been increasing steadily in world auto industries driven mainly by energy savings movement. Numerous types of plastic materials are currently used for various applications. In bumpers and bumper fascias especially, there is considerable competition between reaction injection molded thermoset polyurethane (RIM-PU) and thermoplastic olefin (TPO). However, a major shift from RIM-PU to TPO is taking place for bumper fascias because of weight savings, cost effectiveness and recyclability (Mitra O'Malley and Joel Kopinsky, "Automotive Environmental and Safety Rules are Key Driving Forces for Innovation," Modern Plastics Encyclopedia' 94, pp. 20–22, Mid-November 1993). Based on extensive field studies by TPO manufacturers and their Original Equipment Manufacturer (OEM) partners, however, painted TPO automotive bumper fascias have experienced various dynamic contact induced paint damage during low-level auto to auto impact, door impact, and also, to a lesser extent, from standard projectile impact that occurs during normal driving conditions. The scuff damage of painted thermoplastic bumpers or fascias is a result of compression (indentation) and then subsequent sideways sliding while the two surfaces are still in contact. This damage occurs more readily at the higher temperature range of automotive service environment (i.e., 120° F.–130° F.), particularly for the softer substrates such as elastomer modified TPos. The bumper fascias consist of a plastic substrate with a surface treatment, a thermoplastic adhesion promoter, a primer paint and a top clear coat. Therefore, the coating-substrate structural integrity under dynamic contact exposures is not controlled by a single material or parameter. Recently; OEM's have tried to include the paint damage resistance in the performance specifications of a component as one of the engineering standards due to increasing customer complaints regarding the high paint damage susceptibility of plastic bumper fascias and body panels and the significant repair cost. No meaningful standard procedure is currently available due to the lack of general understanding of the problem and the complex structural composition of the component.

(2) Description of the Related Art

The related art has shown various apparatuses and systems for testing the surface damage resistance, such as scratch resistance of a film or sheet. Illustrative are U.S. Pat. No. 2,311,430 to Beno; U.S. Pat. No. 2,801,540 to Rondeau; U.S. Pat. No. 3,289,458 to Deichert et al; U.S. Pat. No. 4,791,807 to Oechsle and U.S. Pat. No. 5,490,410 to Markstrom.

In particular, U.S. Pat. No. 2,890,585 to Albrecht describes an apparatus for testing the hardness of a coating made of an electrically non-conducting material. The apparatus has an automatic shut-off upon failure or break through of the coating.

In addition, U.S. Pat. No. 3,087,326 to MacDonnell describes an apparatus for determining scuff resistance and/or surface breakdown of various materials by comparing the temperature variations between the contacting surfaces.

Also, U.S. Pat. No. 2,373,200 to Simmons et al describes an apparatus to test scratch adhesion of a panel which moves a stylus along the panel until the stylus penetrates the coating.

Also of interest are U.S. Pat. No. 3,985,026 to Griffin et al and U.S. Pat. No. 5,438,863 to Johnson. Griffin et al describes an apparatus for testing a surface coating on a glass container. The apparatus holds two glass containers and applies a load normal to the second glass container which is transmitted to the first glass container. The containers are then moved relative to each other. Johnson describes a portable testing system for determining material properties of an elastomeric material. The system uses a computer to process digital test data from the load cell of the test fixture and to control the overall test functioning of the system.

Several studies have been conducted on impact or chipping of painted plastic bumpers and bumper fascias. Illustrative are: Oosterbroek, M., and Boomgaard, R., Proceedings of the ACS Division of Polymeric Materials Science and Engineering, V. 58, Published by ACS, pp. 426–430, 1988; A. C. Ramamurthy, W. Isbell, V. Venditto and T. Jennings, SAE Tech Paper No. 932331, Dearborn, Mich. 1994; A. C. Ramamurthy, J. W. Holubka, and Dennis J. Mihora, "Adhesion Mechanics During Low-Speed Normal-Impact of Spherical "Rocks" into Multilayer Painted Steel Substrates," Proceedings of the 18th Annual Meeting of The Adhesion Society, pp. 52–55, 1995) and Gilmer, T. C. and Adesko, P. L., American Institute of Chemical Engineers, Workshop, V. 84, N 260, Published by AIChE, New York, pp. 16–32, 1988) (more relevant to a metal substrate). In addition, a few limited studies on the problems associated with compression-sliding type contact have also been conducted. Illustrative are: E. K. L. Lau, K. Swain, and S. Srinivasan, "Mar Resistance of Polyolefins: Mechanisms, Measurements and Materials," Proc. of The Third International Conference & Exhibit, TPOs in Automotive 1996, Oct. 28–30, 1996, Novi, Mich.; E. Eugene Shin, Charles K. Buehler, Preston W. Vallad, Roger Morgan, Lawrence Drzal, and Stephen M. Dwyer, "Reliability and Durability of Coated Composite Panels for Automotive Applications, "Proc. of The Third International Conference & Exhibit, TPOs in Automotive 1996, Oct. 28–30, 1996, Novi, Mich. and Michelle J. Mikulec and Thomas C. Yu, "Uppermost Stratum Morphology and Paintability of Thermoplastic Olefins", Proc. of The Third International Conference & Exhibit, TPOs in Automotive 1996, Oct. 28–30, 1996, Novi, Mich.

There remains the need for an apparatus and method for determining and quantifying the resistance to scuff damage of paint on a panel which allows for good reproducability and reliability and which uses an actuator to provide constant and accurate pressure.

OBJECTS

It is therefore an object of the present invention to provide an apparatus for use in determining and quantifying the resistance to scuff damage of a film adhered on a panel. Further, it is an object of the present invention to provide an apparatus for use in determining the resistance to scuff damage of a film adhered on a panel which allows for the reproducability and reliability of results. Still further, it is an object of the present invention to provide an apparatus which allows the resistance to scuff damage of a variety of different films adhered on different panels to be determined. Further still, it is an object of the present invention to provide an apparatus which allows the resistance to indention and slide/scuff damage of a film adhered on a panel to be tested and measured. Further, it is an object of the present invention to provide an apparatus for testing the scuff resistance of a film adhered on a panel where the pressure applied between the indentor and the panel during testing is controlled by an air pressure actuator. Still further, it is an object of the present invention to provide a method for determining the resistance to scuff damage of a film adhered on a panel which simulates real service induced damage. Further still, it is an object of the present invention to provide a method for determining the resistance to scuff damage of a film adhered on a panel which quantifies the damage behavior and rates material performance. Still further, it is an object of the present invention to provide a reliable testing apparatus and reproducible testing procedure to access the relative performance of painted plastic substrates during dynamic contact-induced events.

These and other objects will become increasingly apparent by reference to the following drawings and the description.

DETAILED DESCRIPTION OF THE PREFERRED EMBODIMENTS

Figure 1:
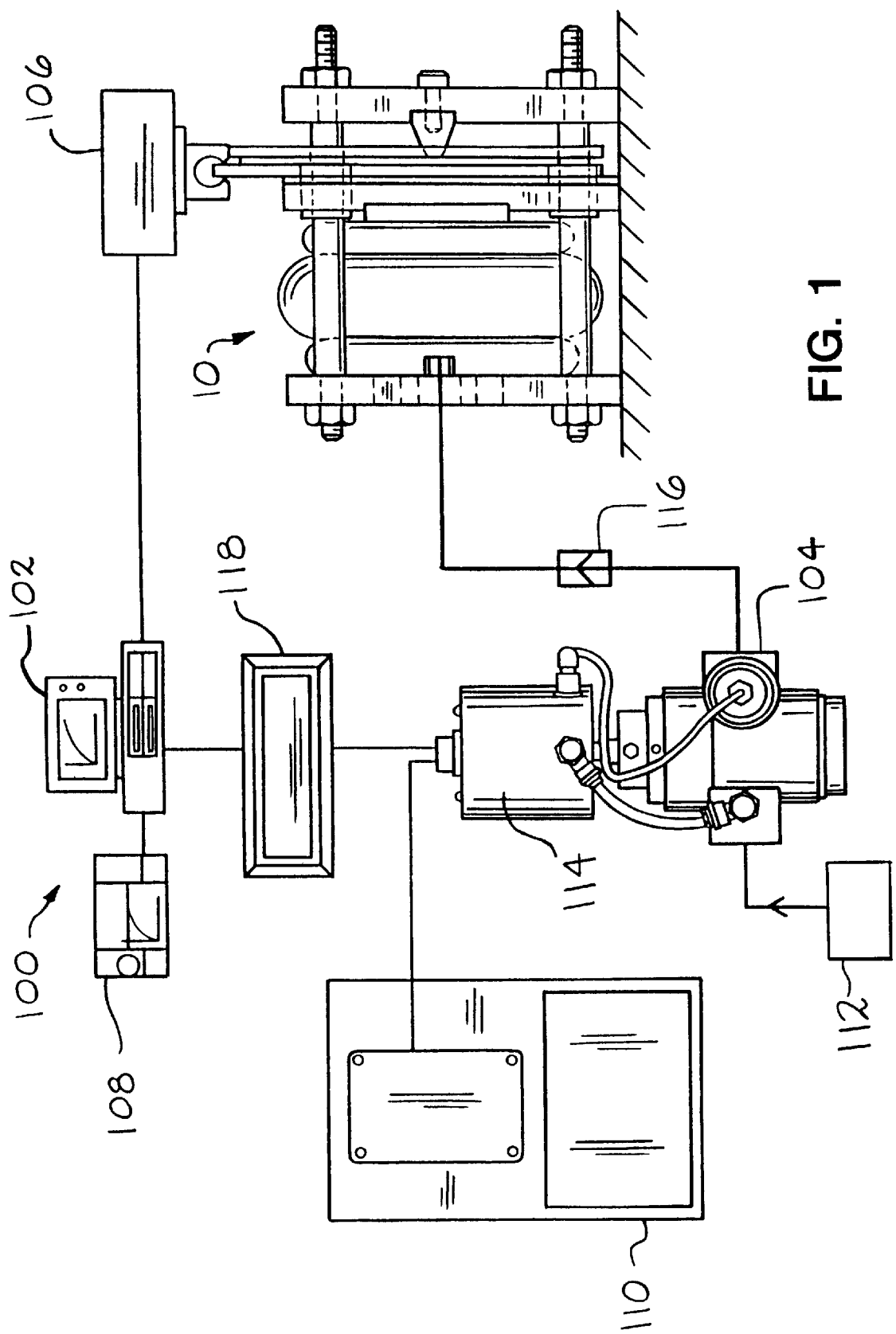
FIG. 1 is a schematic diagram of the indentation-slide testing system 100 of the present invention.

The present invention relates to a test module which mounts in an apparatus for determining resistance to scuff damage of a film adhered on a panel which comprises: frame means which mounts in the apparatus; spaced apart plate means provided on the frame means so that one of the plate means is movable towards and away from the other on the frame means and with opposed parallel faces on each of the plate means; an indentor means with a rounded tip provided on one of the faces of the plate means; and activator means mounted on the frame means so as to move the one of the plate means towards the other of the plate means, wherein activator means provides a preselected load per unit area by the indentor means on the film.

Further, the present invention relates to a testing apparatus for determining resistance to scuff damage of a film adherent on a substrate of a panel, which comprises: a test module apparatus means which comprises: (1) frame means; (2) spaced apart plate means provided on the frame means so that one of the plate means is movable towards and away from the other of the plate means on the frame means and with opposed parallel faces on each of the plate means; (3) an indentor means with a rounded tip provided on one of the faces of the plate means; and (4) activator means mounted on the frame means so as to move the one of the plate means towards the other of the plate means, wherein movement of the activator means is provided by a fluid inside bellows in the activator means which provides a preselected load per unit area by the indentor means on the film; motive means for moving the panel in the test module apparatus means between the plate means with the indentor means against the film; gauge means for determining the load per unit area applied by the indentor means on the film; and supply means for introducing the fluid into the bellows of the activator means.

Still further, the present invention relates to a test module which mounts on an apparatus for determining resistance to scuff damage of a film adhered on a substrate of a panel which comprises: an indentor with a rounded tip on a first side positionable against the film on the substrate; an indentor support plate with a planar face which mounts the indentor on a second side of the indentor opposite the first side with the tip; parallel rods mounted on the indentor support plate perpendicular to the planar face; a movable plate mounted on the rods so as to be movable towards and away from the indentor support plate with a planar face parallel to the planar face of the support plate and perpendicular to the rods, wherein the panel is supported for movement in a space between the movable plate and the indentor support plate with the indentor against the film; an end plate mounted on the rods spaced from the space between the movable plate and indentor support plate so as to hold the rods in position for movement of the movable plate; a stroke activator mounted between the end plate and the movable plate, wherein movement of the stroke activator is produced by providing a fluid inside bellows in the activator which moves the movable plate towards the indentor to produce preselected loads per unit area of the indentor against the film and then the film is moved against the indentor to determine scuff damage.

Further still, the present invention relates to a testing apparatus for determining resistance to scuff damage of a film adhered on a panel which comprises: a test module which comprises: (1) an indentor with a rounded tip on a first side positionable against the film on the panel; (2) an indentor support plate with a planar face which mounts the indentor on a second side of the indentor opposite the first side with the tip; (3) parallel rods mounted on the indentor support plate perpendicular to the planar face; (4) a movable plate mounted on the rods so as to be movable towards and away from the indentor support plate with a planar face parallel to the planar face of the support plate and perpendicular to the rods, wherein in use the panel is supported for movement in a space between the movable plate, and the indentor support plate with the indentor against the film; (5) an end plate mounted on the rods spaced from the space between the movable plate and indentor support plate so as to hold the rods in position for movement of the movable plate; (6) a stroke activator mounted between the end plate and the movable plate, wherein movement of the stroke activator is produced by providing a fluid inside bellows in the activator which moves the movable plate towards the indentor to produce preselected loads per unit area of the indentor against the film and then the film is moved against the indentor to determine scuff damage; motive means for moving the panel in the test module; gauge means for determining the load per unit area applied by the indentor plate with the indentor on the film; and supply means for introducing the fluid into the bellows of the activator at a pressure which provides the load per unit area.

Finally, the present invention relates to a method of testing for resistance to scuffing of a film adhered on a substrate of a panel, which comprises: providing a testing apparatus for determining resistance to scuff damage of the film adherent on a panel which comprises: a test module apparatus which comprises frame means; spaced apart plate means provided on the frame means so that one of the plate means is movable towards and away from the other plate means on the frame means and with opposed parallel faces on each of the plate means; an indentor means with a rounded tip provided on one of the faces of the plate means; and activator means mounted on the frame means so as to move the one of the plate means towards the other of the plate means, wherein the activator which provides a preselected load per unit area by the indentor means on the film; motive means for moving the panel in the test module between the plate means with the indentor means against the film; and gauge means for determining the load per unit area applied by the indentor means against the film; moving the panel between the plate means with the indentor means against the film on the substrate of the panel; determining the scuff resistance of the film on the substrate of the panel as a function of the load per unit area applied on the film by the indentor.

FIG. 1 shows the indentation-slide testing system 100 of the present invention. The system 100 is used to determine and quantify the resistance to scuff damage of a film or coating 152 on a substrate 150 of a panel 154. In the preferred embodiment, the substrate 150 is constructed of either an injection molded thermoset polyurethane (RIM-PU) or thermoplastic olefin (TPO) and the film or coating 152 is paint. However, the substrate 150 could also be constructed of a metal and the coating 152 could also contain metal or could be various polymers. It is also possible that the system 100 could be used with an uncoated substrate (not shown) constructed of a metal or plastic. Preferably, the test panels 154 are similar to those used in the auto industry such as for bumpers and bumper fascias. The bumper fascias consist of a plastic substrate with a surface treatment of a thermoplastic adhesive or adhesion promoter, a primer or base paint and a top clear coat. In the preferred embodiment, the adhesion promoter has a dry film thickness of 0.3 mil (8 $\mu$m), the base coat dry film thickness is 1.6 mil (41 $\mu$m) and the dry film thickness of the clear coat is 1.6 mil (41 $\mu$m). Thus, the total dry film thickness of the paint is 3.5 mil (89 $\mu$m). The substrates preferably have a size of 4.0 inch (10 cm)×6.0 inch (15 cm) and a thickness of 0.125 inch (0.32 cm). The system 100 includes a computer 102, pressure control valves 104 and a testing module 10. The computer 102 controls the entire system loo and also collects and displays the results of the testing. The computer 102 preferably reads the testing results from the load cell 106 of the testing module 10 (to be described in detail hereinafter). The load cell 106 preferably provides a signal to the computer 102. A plotter 108 is preferably provided for printing a hard copy of the results of the testing. The indentation load of the testing module 10 is controlled by the high precision proportional pressure control valves 104 such as BB2/PSR Servo valves manufactured by Proportion Air Inc. The pressure control valves 104 are controlled by a voltage potentiometer 110 or alternately, a programmable multitasking controller (not shown) such as the SLC500 manufactured by Allen-Bradley Co., Inc. The media pressure supply 112 for providing the indentation load is preferably of any well known type such as compressed air. The power supply 114 for the system 100 is preferably included with the voltage potentiometer 110 or the programmable multitasking controller. A pressure rate control needle valve 116 is located between the pressure control valves 104 and the testing module 10 to control the indentation loading rate. The pressure control valves 104 are also provided with a digital pressure indicator 118 which enables a user to monitor the pressure or load being provided to the testing module 10.

Figure 2:
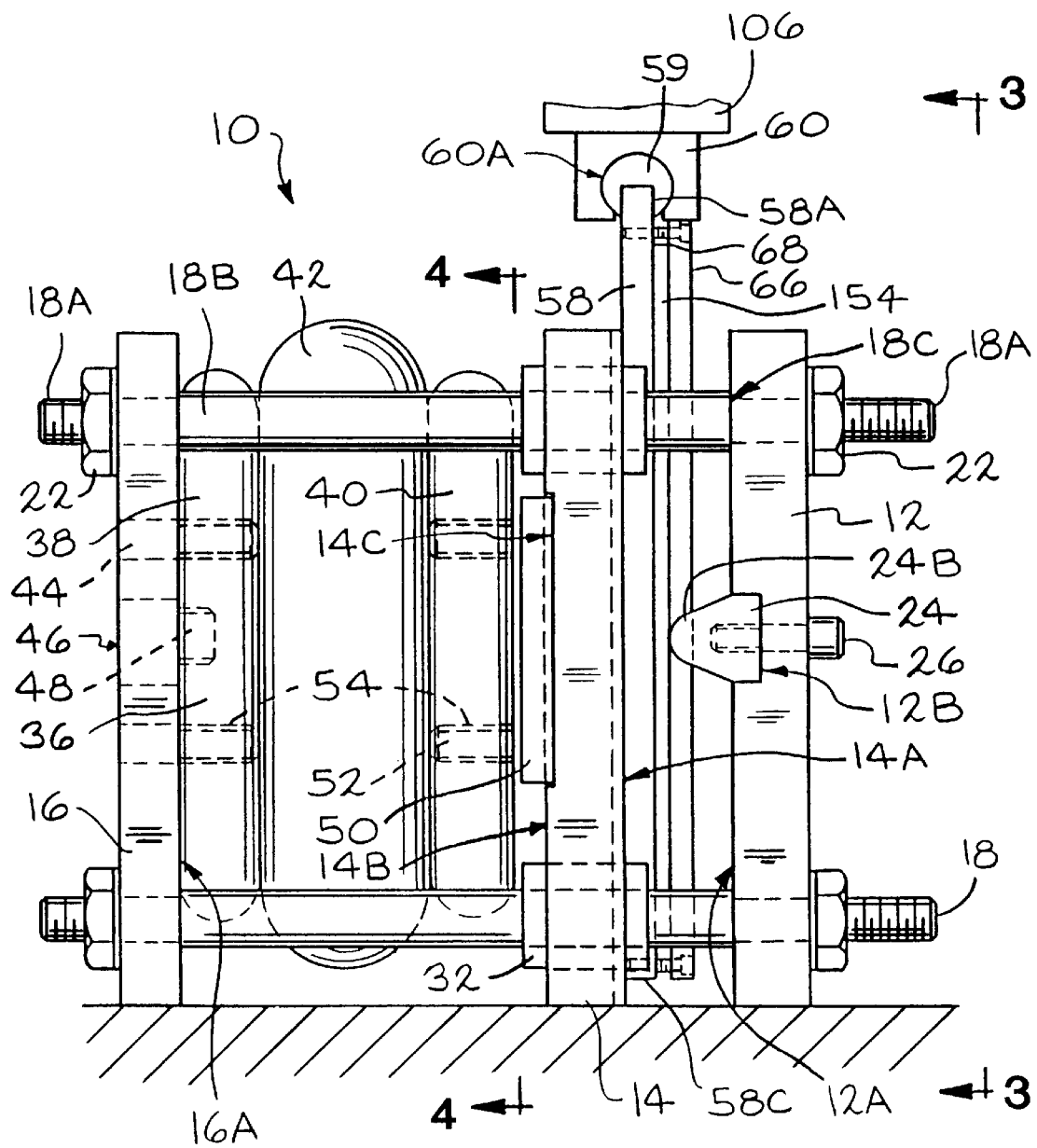
FIG. 2 is a front view of the indention-slide test module 10 showing the indentor 24, the indentor support plate 12, the compression moving plate 14 and the end plate 16.
Figure 3:
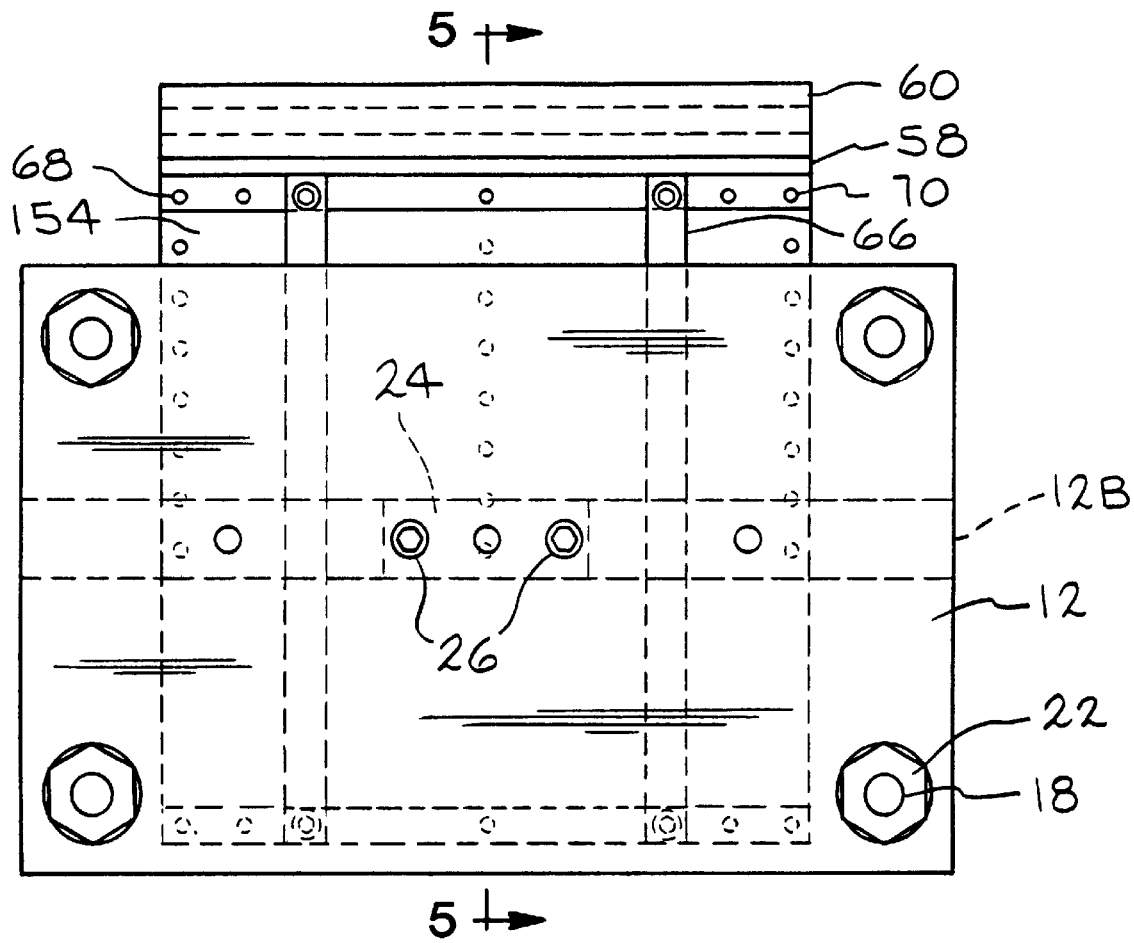
FIG. 3 is a side view of the testing module 10 along the line 3—3 of FIG. 2 showing the indentor support plate 12, the support rods 18, the sliding panel support plate 58 and the panel 154.
Figure 4:
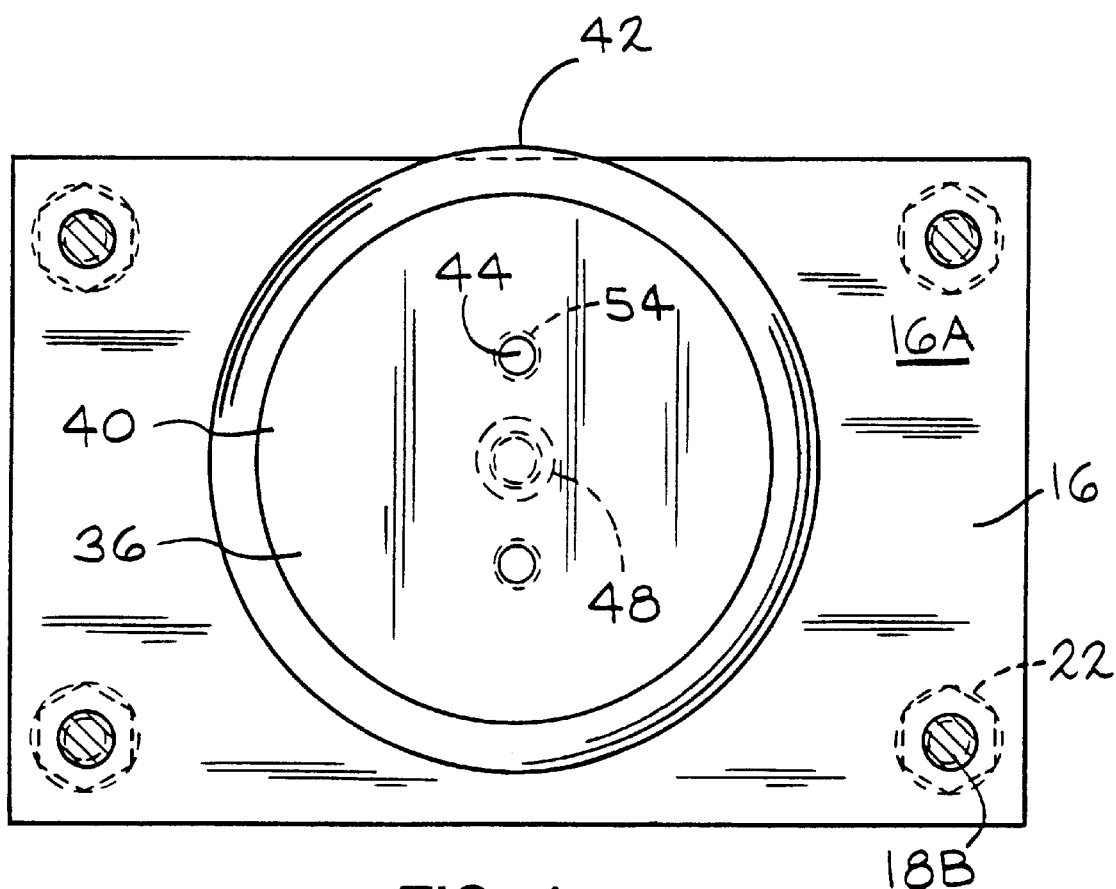
FIG. 4 is a cross-sectional view of the test module 10 along the line 4—4 of FIG. 2 showing the actuator 36 and the end plate 16.
Figure 8:
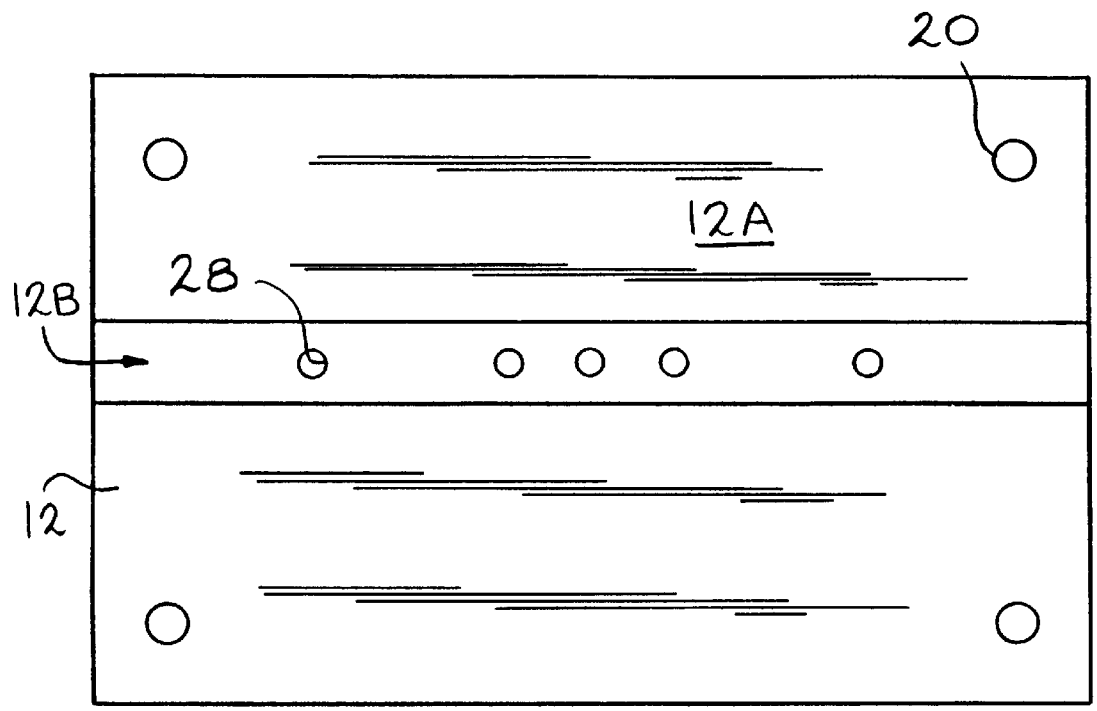
FIG. 8 is a side view of the indentor support plate 12 showing the groove 12B and the mounting holes 20 for the indentor 24.
Figure 14:
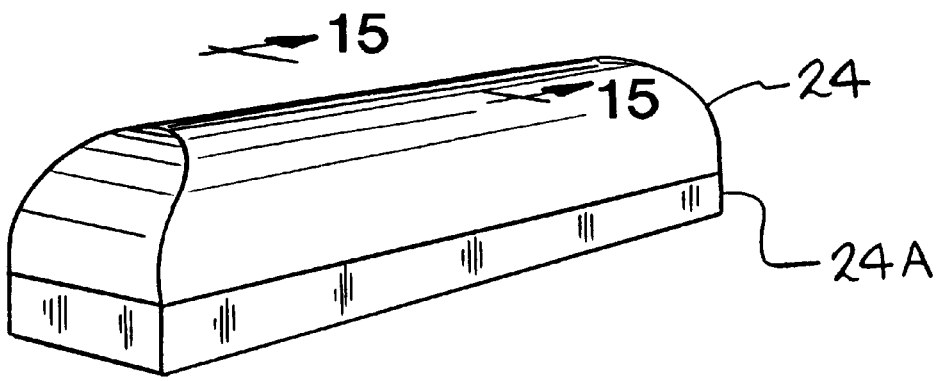
FIG. 14 is a perspective view of the indentor 24 of the first embodiment.
Figure 15:
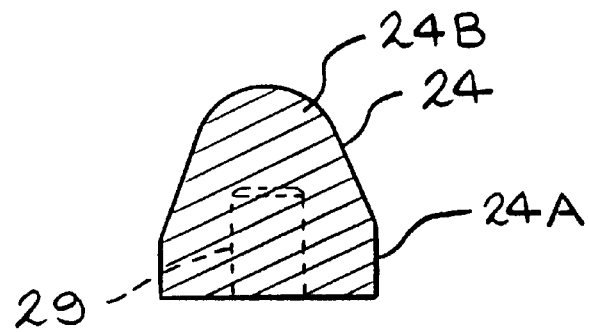
FIG. 15 is a cross-sectional view of the indentor 24 of FIG. 15 along the line 15—15 showing the rectangular base 24A and the arcuate top portion 24B.
Figure 16:
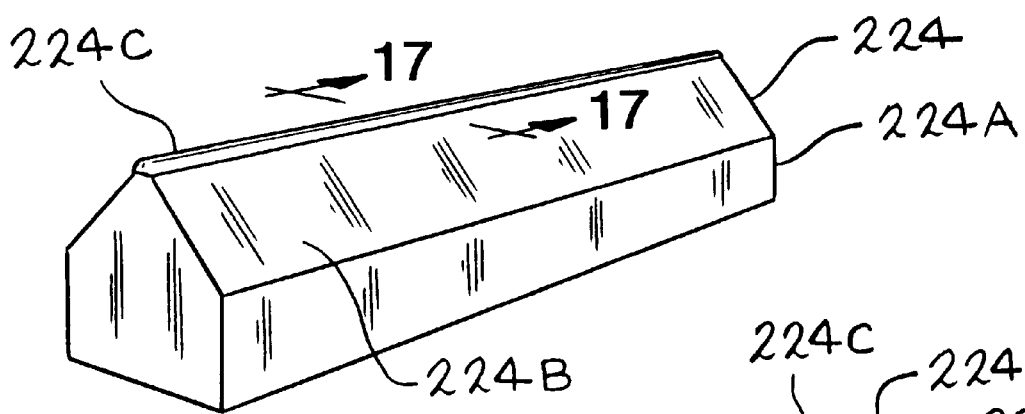
FIG. 16 is a perspective view of the indentor 224 of the second embodiment.
Figure 17:
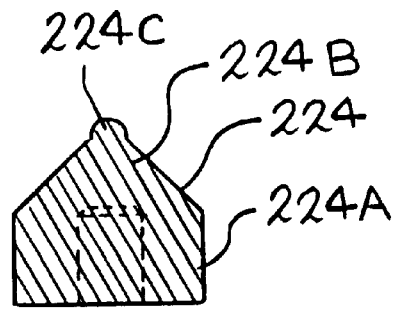
FIG. 17 is a cross-sectional view of the indentor 224 of FIG. 16 along the line 17—17 showing the rectangular base 224A and the angled top portion 224B with the arcuate tip 224C.

As shown in FIG. 2, the testing module 10 includes an indentor support plate 12 with an indentor 24, a sliding panel support plate 58 for holding the test panel 154, a compression moving plate 14, a load or pressure actuator 36 and an end plate 16. The plates 12, 14 and 16 are preferably similar in shape and size. Preferably, the plates 12, 14 and 16 have a rectangular shape with a thickness of 0.625 inches (1.6 cm). In the preferred embodiment, the indentor support plate 12, the compression moving plate 14 and the end plate 16 are mounted parallel to each other such that the inner and outer surfaces 12A, 14A, 16A and 14B, 16B of the plates 12, 14 and 16 are parallel. The plates 12, 14 and 16 are connected together by four support rods 18 located at the four corners of the plates 12, 14 and 16 (FIG. 2). However, it is understood that the plates 12, 14 and 16 can be mounted together by any other well known means. In the preferred embodiment, the indentor support plate 12 and the end plate 16 are mounted on opposite ends 18A of the support rods 18. The indentor support plate 12 and the end plate 16 are preferably similarly mounted and are both fixably mounted on the support rods 18. In the preferred embodiment, the ends 18A of the support rods 18 are threaded and have a diameter slightly smaller that the unthreaded portion 18B of the rods 18. The threaded ends 18A of the rods 18 are preferably extended through mounting holes 20 in the indentor support plate 12 and the end plate 16 such that the unthreaded portion 18B of the rods 18 extend between the two plates 12 and 16. Nuts 22 are secured on the threaded ends 18A of the rods 18 to keep the plates 12 and 16 on the rods 18. In addition, the shoulders 18C formed between the threaded end 18A and the unthreaded portion 18B of the support rods 18 act as a stopper to prevent the plates 12 and 16 from moving inward toward each other. In the preferred embodiment, the plates 12 and 16 are spaced a distance of 4.5 inches (11.43 cm) apart. The indentor support plate 12 and the end plate 16 are preferably constructed of tool steel. The inner surface 12A of the indentor support plate 12 is provided with a groove 12B which extends horizontally along the entire width of the plate 12 (FIG. 8). The groove 12B is preferably positioned in the vertical center of the plate 12. The indentor 24 is mounted in the groove 12B of the indentor support plate 12. The indentor 24 is preferably mounted in the center of the groove 12B and is secured to the plate 12 by two bolts 26 which extend through holes 28 in the indentor support plate 12 and thread into holes 29 in the indentor 24 to secure the indentor 24 in the groove 12B in the indentor support plate 12 (FIG. 3). The indentor 24 can have a variety of different shapes depending upon the specific test to be performed. Preferably, the indentor 24 has a length between 2.5 to 6.0 inches (6.3 to 15.0 cm) and a width of approximately about 0.75 inch (1.91 cm). The arcuate shaped top portion 24B preferably has a radius from 0.005 to 0.25 inches (0.0127 to 0.64 cm). In the first embodiment, the indentor 24 has a rectangular base 24A and an arcuately shaped top portion 24B (FIGS. 14 and 15). In a second embodiment, the indentor 224 has a rectangular block base 224A with an angled top portion 224B which has an arcuate tip 224C (FIGS. 16 and 17). The indentor 224 of the second embodiment preferably has a length of 2.8 inches (7.0 cm) a width of approximately about 0.75 inch (1.91 cm) with a 0.0625 inch (0.15.88 cm) radius tip 224C. The exact length of the indentor 24 or 224 and the shape of the top portion 24A or 224A or tip 224C depends on the particular test being performed and the construction of the panel 154. The indentor 24 or 224 is preferably constructed of a tool steel, an aluminum or plastic with or without coating on surface. In addition, the coating on the surface of the indentor 24 or 224 can be constructed of a similar paint material used in the film 152 of the test panels 154.

Figure 6:
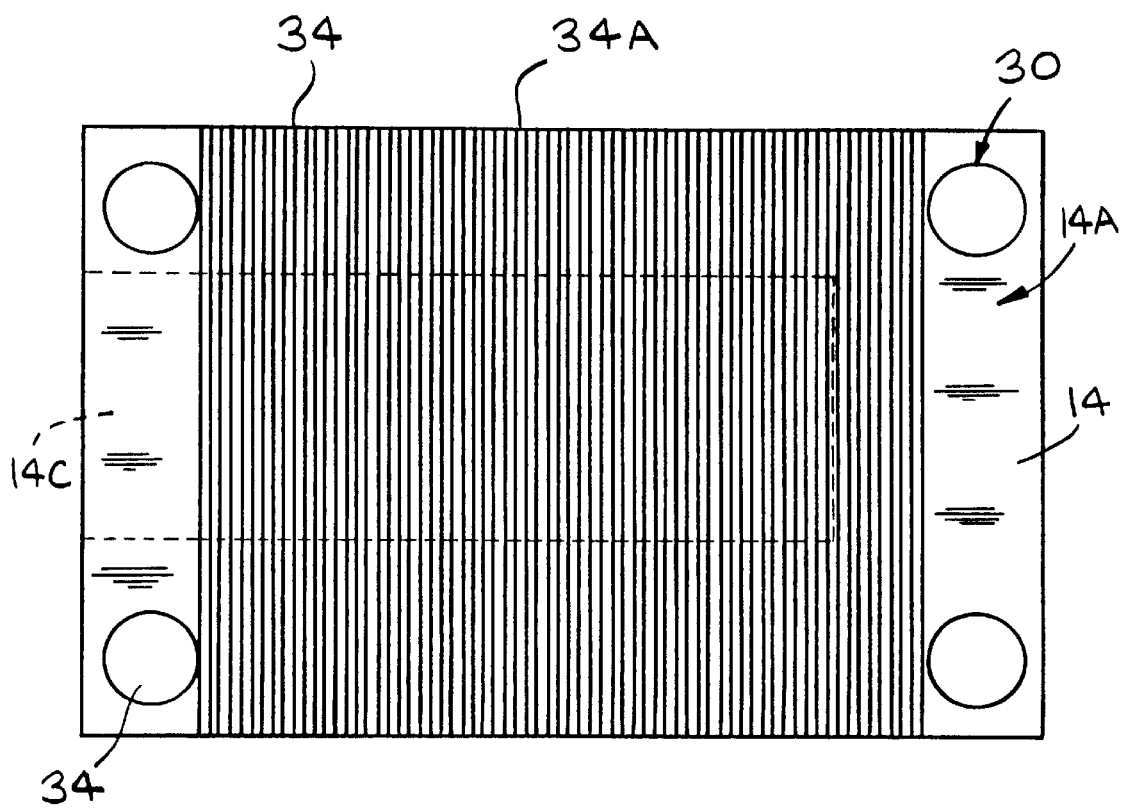
FIG. 6 is a side view of the compression moving plate 14 showing the grooves 14C.
Figure 7:
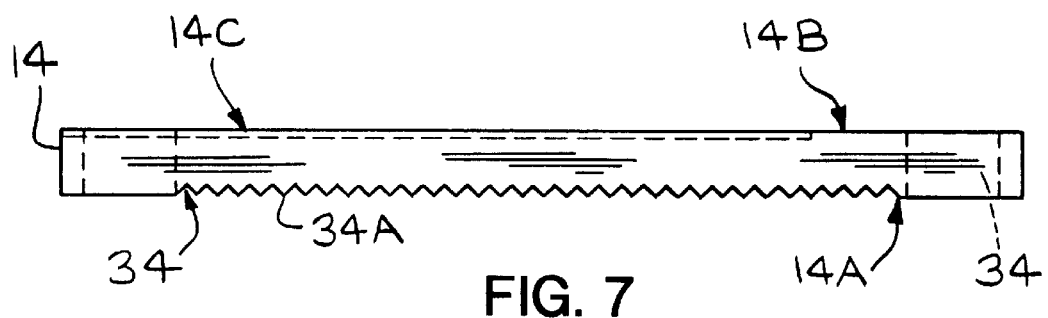
FIG. 7 is a top view of the compression moving plate 14 showing the grooves 14C.

The compression moving plate 14 is preferably slidably mounted on the support rods 18 between the indentor support plate 12 and the end plate 16. The compression moving plate 14 has four mounting holes 30 at each corner. The four holes 30 each have a linear bearing 32 mounted within the hole 30 which allows the compression moving plate 14 to move smoothly and easily along the unthreaded portion 18B of the rods 18. In the preferred embodiment, the support rods 18 have a circular cross-section which allows for easier movement of the compression moving plate 14. The inner surface 14A of the compression moving plate 14 adjacent the indentor support plate 12 is preferably provided with grooves 34 extending vertically between the top and bottom of the plate 14 (FIGS. 6 and 7). The grooves 34 preferably have a width of 0.1875 inches (0.476 cm) peak 34A to peak 34A. The grooves 34 extend in the direction of movement of the panel 154 during testing and reduce the total amount of surface area of the compression moving plate 14 in contact with the panel 154 during testing which reduces the amount of friction between the plate 14 and the panel 154 when the panel 154 is moved. The compression moving plate 14 is preferably constructed of tool steel; however, other materials such as aluminum or other metals or plastics could also be used. In addition, the peaks 34A on the inner surface 14A of the plate 14 could be coated with a material to reduce friction between the plate 14 and the panel 154.

Figure 5:
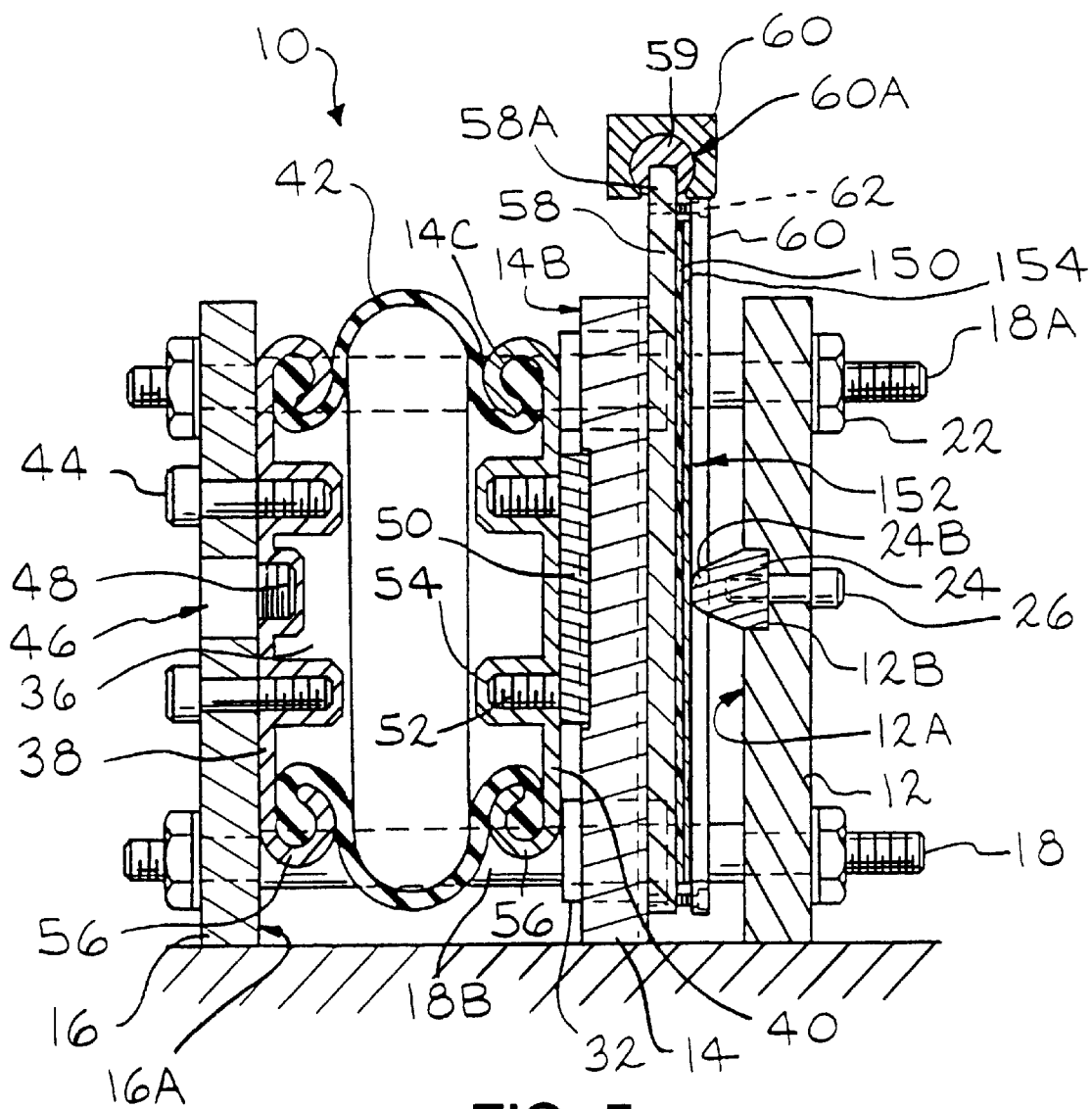
FIG. 5 is a cross-sectional view of the testing module 10 along the line 5—5 of FIG. 3 showing the panel 154 between the indentor support plate 12 and the compression moving plate 14 and the actuator 36 adjacent the compression moving plate 14.
Figure 9:
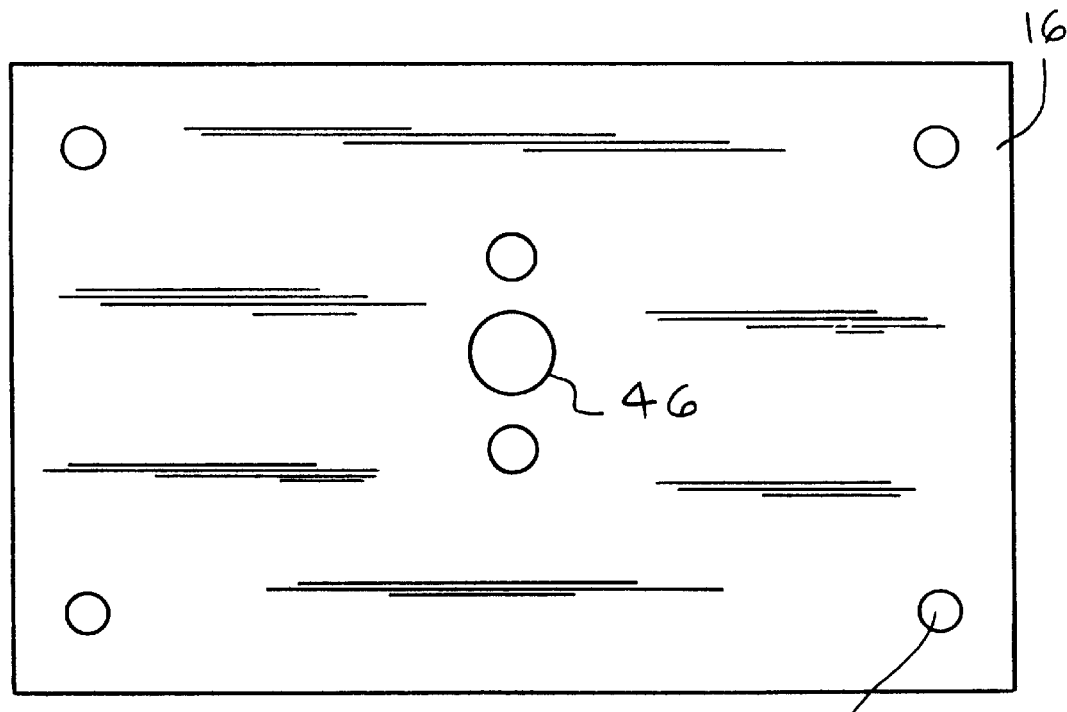
FIG. 9 is a side view of the end plate 16.

The load or pressure actuator 36 for providing the load in the testing module 10 is mounted between the end plate 16 and the compression moving plate 14. The actuator 36 is preferably mounted slightly off-center between the plates 14 and 16 such that the actuator 36 extends above the tops of the plates 14 and 16. The actuator 36 is preferably fluid activated and includes an upper plate 38 and a lower plate 40 with bellows 42 located therebetween. The upper plate 38 is preferably mounted by bolts 44 to the inner surface 16A of the end plate 16 (FIG. 5). The end plate 16 has an opening 46 spaced between the bolts 44 which is in fluid communication with an air inlet 48 for the bellows 42 (FIGS. 5, 6 and 9). The lower plate 40 of the actuator 36 is preferably adjacent the outer surface 14B of the compression moving plate 14. A spacer 50 is provided between the lower plate 40 of the actuator 36 and the compression moving plate 14. The spacer 50 is mounted on the lower plate 40 of the actuator 36 by bolts 52. The spacer 50 allows for the linear bearings 32 of the compression moving plate 14 and prevents the lower plate 40 from contacting the bearings 32. The outer surface 14B of the compression moving plate 14 is provided with a horizontal groove 14C into which the spacer 50 is mounted. The groove 14C extends from one side of the compression moving plate 14 toward the other side. However, preferably the groove 14C does not extend the entire length of the compression moving plate 14 but is positioned at one side. Due to the positioning of the actuator 36, between the plates 14 and 16, the spacer 50 is not positioned in the center of the compression moving plate 14 but is spaced slightly toward the top. The bolts 44 and 52 mounting the upper and lower plates 38 and 40 of the actuator 36 to the end plate 16 and the compression moving plate 14 thread into close ended passageways 54 in the plates 38 and 40. The close ended passageways 54 prevent the ends of the bolts 44 and 52 from interfering with the bellows 42 (FIG. 5).

The upper and lower plates 38 and 40 of the actuator 36 are held together by the arcuate flexible bellows 42. The bellows 42 are mounted beneath flange clips 56 which extend along the top and bottom of the plates 38 and 40 (FIG. 5). The bellows 42 are preferably constructed of two-ply rubber; however, other resilient and flexible material could also be used. In the preferred embodiment, the actuator 36 is an AIRSTROKE® actuator as manufactured by Firestone, located in Akron, Ohio. Table 1 is the force table for two models of the AIRSTROKE® actuator.

Force Table

| Assembly Height (in.) | Volume @ 100 PSIG (in³) | Pounds Force | | | | |
|---|---|---|---|---|---|---|
| | | @ 20 PSIG | @ 40 PSIG | @ 60 PSIG | @ 80 PSIG | @ 100 PSIG |
| 3.0 | 32 | 220 | 420 | 640 | 880 | 1,120 |
| 2.0 | 17 | 350 | 680 | 1,020 | 1,370 | 1,720 |

Figure 11:
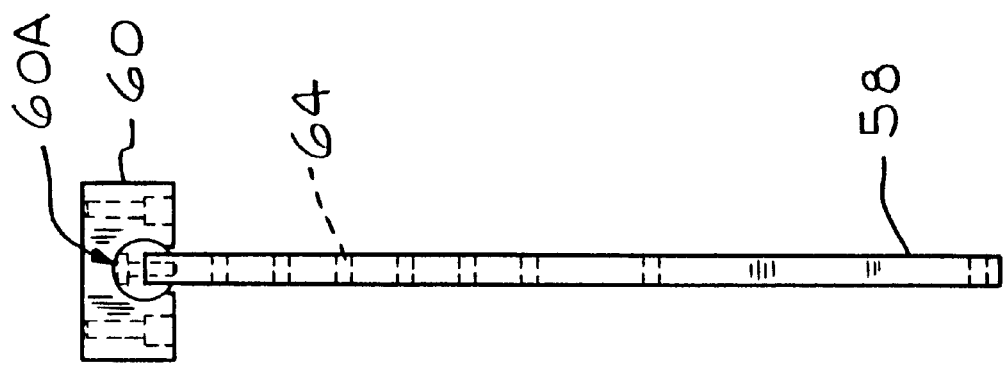
FIG. 11 is a front view of the panel support plate 58 showing the bracket 60.
Figure 10:
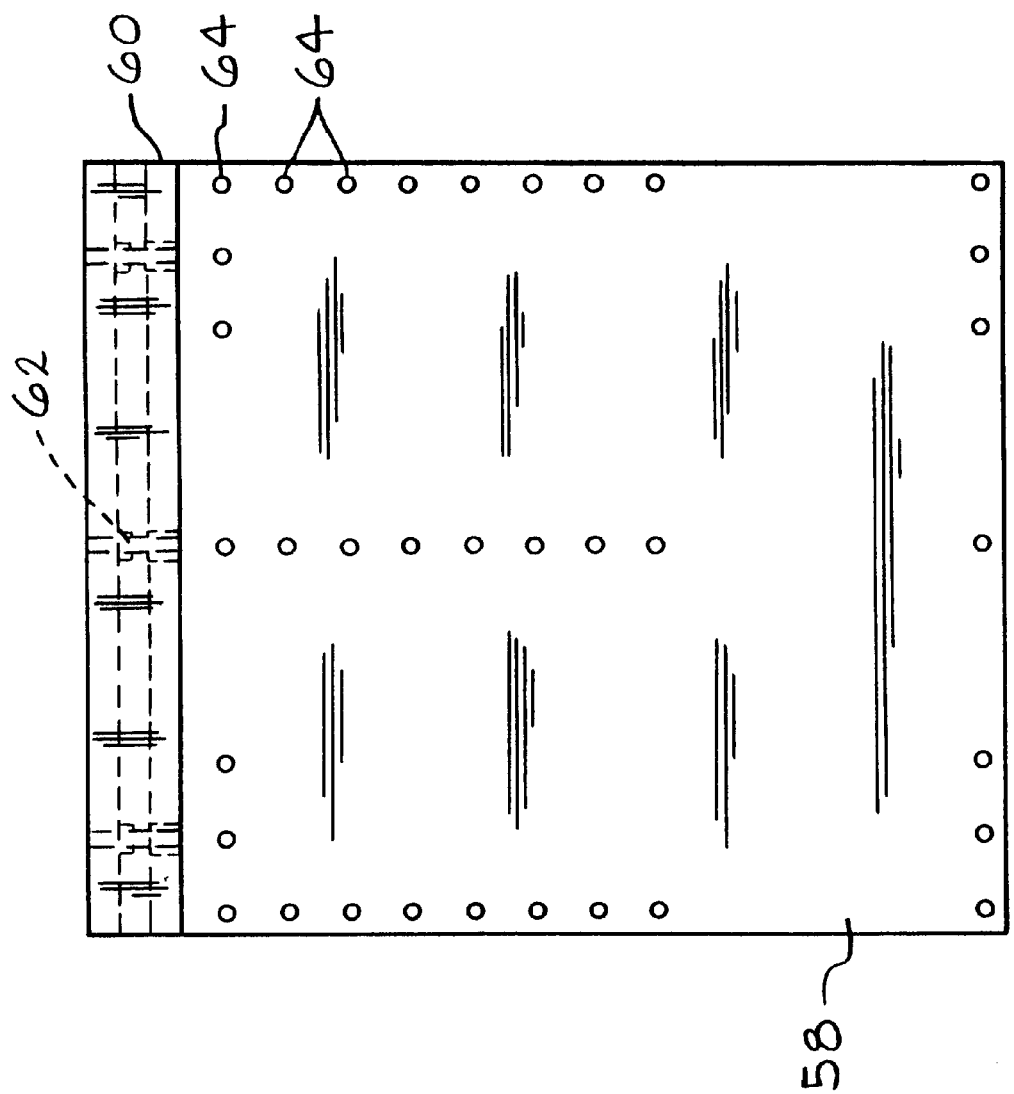
FIG. 10 is a side view of the panel support plate 58.
Figure 12:
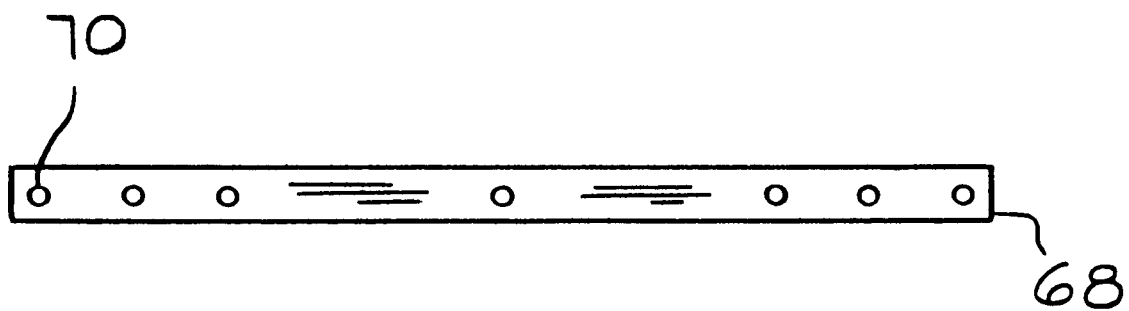
FIG. 12 is a side view of the panel guide rods 68.
Figure 13:
FIG. 13 is a side view of the panel mounting rods 66.

A sliding panel support plate 58 is preferably mounted between the indentor support plate 12 and the compression moving plate 14 (FIGS. 2 and 5). The sliding panel support plate 58 preferably extends parallel to the plates 12, 14 and 16 and particularly, to the inner surface 14A of the compression moving plate 14. In the preferred embodiment, the sliding panel support plate 58 has a rectangular shape with a size such that the plate 58 easily fits within the space between the support rods 18. The support plate 58 is of such a height as to extend above the top of the other plates 12, 14 and 16 and the actuator 36. The top 58A of the panel support plate 58 is provided with a cylindrical protrusion 59 extending along the horizontal width of the top 58A of the plate 58. The protrusion 59 is mounted onto the top 58A of the plate 58 by bolts 62 which are counter sunk into the top of the protrusion 59 (FIG. 11). The protrusion 59 on the top 58A of the panel support plate 58 is slidably mounted in a circular groove 60A extending along the bottom of a bracket 60. The cylindrical protrusion 59 mounted in the circular groove 60A allows the plate 58 to pivot slightly toward and away from the indentor 24 or 224. This slight movement allows for minor misalignment of the panel support plate 58 or the panel 154 and allows the panel 154 to be perpendicular to the indentor 24 or 224 during testing. The bracket 60 acts to hold the support plate 58 in a vertical position parallel to the other plates 12, 14 and 16. The top of the bracket 60 is mounted on and connected to a load cell 106 which allows for moving the panel support plate 58 and for measuring the load applied to the panel 154. The panel support plate 58 is preferably provided with a series of threaded holes 64 which allow for securing panel mounting rods 66 (FIG. 13) and panel guide rods 68 (FIG. 12) on the plate 58 (FIGS. 3 and 10). The pair of panel guide rods 68 are preferably mounted along the top and bottom edge 58A and 58C of the support plate 58 and extend across the entire width of the support plate 58 (FIGS. 3 and 12). The panel guide rods 68 preferably have an elongate rectangular shape with several holes 70 along the length of the rods 68. The holes 70 allow for mounting the panel mounting rods 66 at different positions on the support plate 58. The guide rods 68 preferably have a thickness of 0.094 inches (0.238 cm) and act to move the mounting rods 66 away from the support plate 58. The panel mounting rods 66 are preferably removably mounted on the side of the support plate 58 adjacent the indentor support plate 12 and extend the entire height of the panel support plate 58. In the preferred embodiment, the panel 154 is mounted between the panel support plate 58 and the mounting rods 66. Preferably, the thickness of the guide rods 68 is equal to or slightly less than the thickness of the panel 154 such that the panel 154 is securely held between the guide rods 68 and the panel support plate 58. The panel 154 is mounted on the panel support plate 58 so that the film or paint 152 is adjacent the indentor 24.

In Use

The system 100 of the present invention is fully instrumented to control and monitor a precise indentation load during the test. The system 100 includes a semi-automatic control and monitoring mechanism for the indentation loading. The system 100 uses a single indentor 24 or 224 to increase the consistency of the testing, and in the overall structural integrity of the indentor 24 or 224. The system 100 allows at least four indentation-sliding tests to be performed on one test panel 154 which improves the reliability of the test by eliminating test panel 154 or setup variability. The system 100 allows accurate control and monitoring of indentation force, which includes versatile indentation loading modes, flexible loading sequence adjustment between indentation loading and sliding, monotonical increase of indentation force during sliding (with various loading rates) and cyclic indentation loading during sliding.

The system 100 allows the damage modes and threshold conditions to be characterized and quantified in terms of (i) various test variables such as temperature, slide speed, indentation load level, indentor materials or surface condition, indentor geometry (radius and length), etc, (ii) materials variables, i.e., types of substrates 150 and associated films or coatings 152, and (iii) process variables. It has been suggested that important parameters controlling scuff damage factors are coefficient of friction, adhesion, substrate composition (stiffness and cohesive strength) (Rose A. Ryntz, "The Influence of Surface Morphology on The Adhesion of Coatings to Thermoplastic Polyolefins Under Stress," Proceedings of the 18th Annual Meeting of The Adhesion Society, pp. 267–273, 1995)) and, also to a lesser extent, coating stiffness and strength. The system 100 allows the most critical parameters and their interactions to be identified and measured.

Scuff damage occurs more readily and excessively at higher temperatures and at higher coefficients of friction. (E. Eugene Shin, Charles K. Buehler, Preston W. Vallad, Roger Morgan, Lawrence Drzal, and Stephen M. Dwyer, "Reliability and Durability of Coated Composite Panels for Automotive Applications, "Proc. of The Third International Conference & Exhibit, TPOs in Automotive 1996, Oct. 28–30, 1996, Novi, Mich.). In addition, the threshold at which damage occurs is at higher load levels with higher slide speed. It is believed that the higher speed reduces the dynamic friction provided the indentation force is constant. In addition, modifying the substrate composition or paint or coating type to reduce friction and/or to increase substrate stiffness improved performance significantly. Furthermore, the scuff damage is not controlled by any single parameter or factor but by a combination of various parameters in synergistic ways. It is necessary to separate out the combined behavior and subsequently, to quantify the effect of individual controlling parameters in a more controlled manner in order to develop a meaningful performance prediction model.

Figure 18:
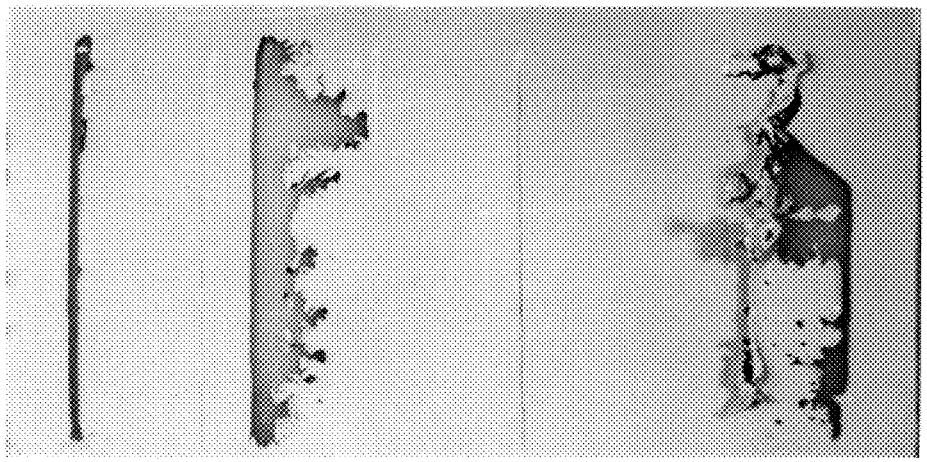
FIG. 18 is an optical micrograph showing the peeled-off scuff (Mode I) produced on Panel BB using an indentor 224 having a top portion radius of 0.0625 inch (0.1588 cm).
Figure 19:
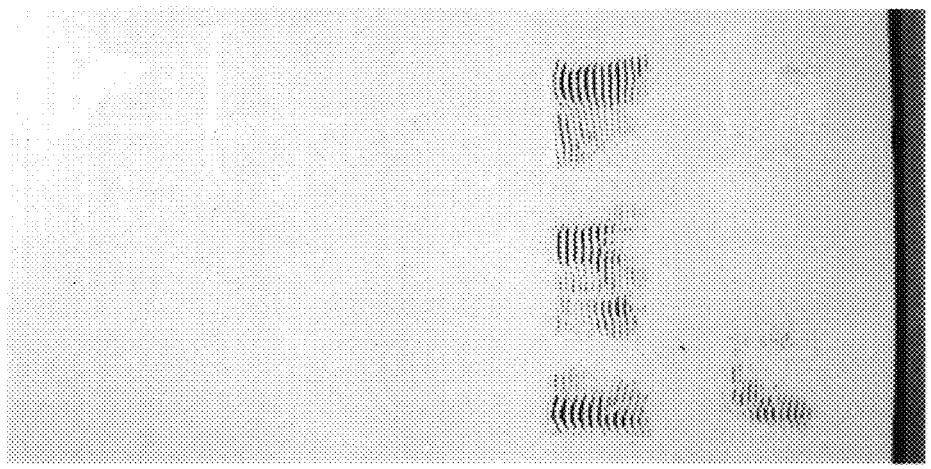
FIG. 19 is an optical micrograph showing the corrugated scuff (Mode II) produced on Panel N using an indentor 224 having a top portion radius of 0.0625 inch (0.1588 cm).
Figure 20:
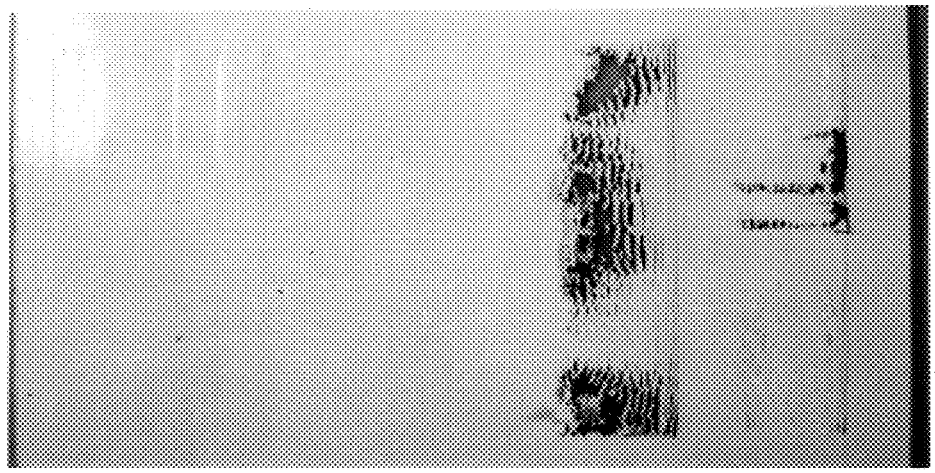
FIG. 20 is an optical micrograph showing a mixed peeled-off and corrugated scuff produced on Panel AB using an indentor 224 with a top portion radius of 0.0625 (0.1588 cm).
Figure 21A:
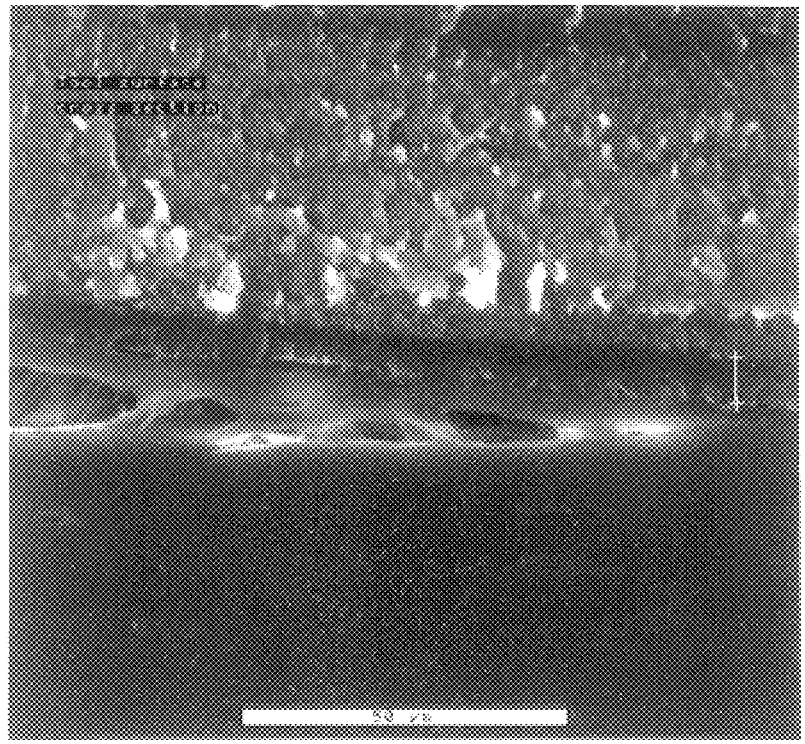
FIG. 21A is an ESEM micrograph at magnification 750× of a cross-sectional view of the Panel BB used in Mode I showing cohesive failure.
Figure 21B:
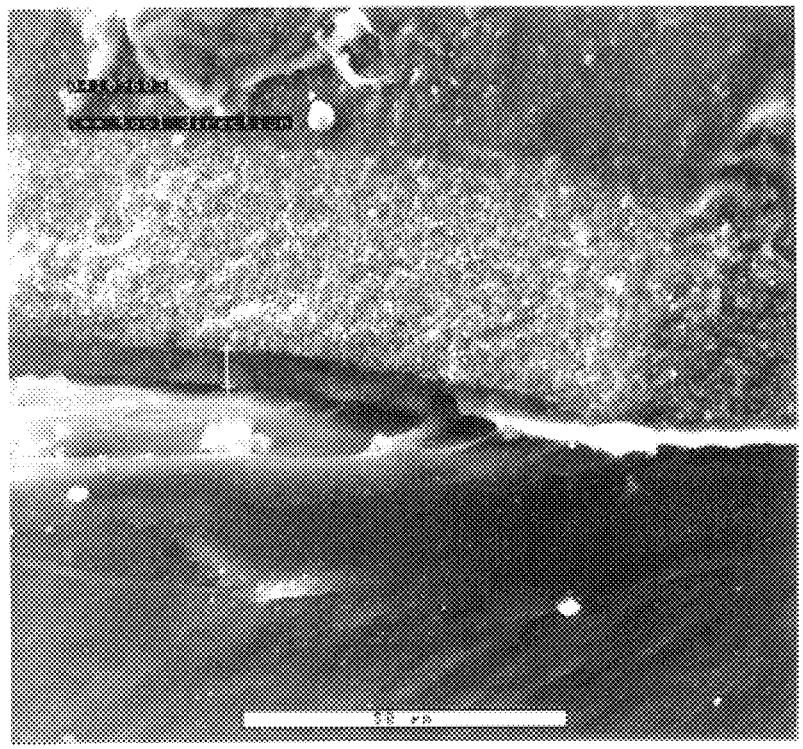
FIG. 21B is an ESEM micrograph at magnification 750× of a cross-sectional view of the Panel BB of Mode I showing adhesion failure.

As shown in FIGS. 18–20, in general there are two (2) distinct scuff damage modes, the peeled-off scuff (Mode I) and the corrugated scuff (Mode II), as well as a mixture of both. Mode I normally occurs on softer TPO substrates and the damage is continuous and covers a larger area. From Environmental Scanning Electron Microscope (ESEM) analysis on cross-sectional views of the damage, the onset failure mode of Mode I scuff damage is either cohesive, (FIG. 21A) or adhesive, (FIG. 21B). As shown in FIG. 21A, the onset of the scuff damage occurs at about 5 $\mu$m below the adhesion promoter layer of the film 152. This suggests that the cohesive strength of the substrate 150, especially at or near the interface of the substrate 150 and the film 152, is critical in determining scuff damage resistance of coated plastic panels 154. It is known that the cohesive strength at the interphase can be affected by molding and painting processes, e.g., injection molding induced skin-core microstructure or residual solvent attack. The scuff damage was clearly a shear failure as indicated by the orientation of the fibrils. Mode I scuff damage is mainly due to high substrate deformation under indentation loading. The scuff damage resistance of the softer substrates 150 was generally low.

Figure 22A:
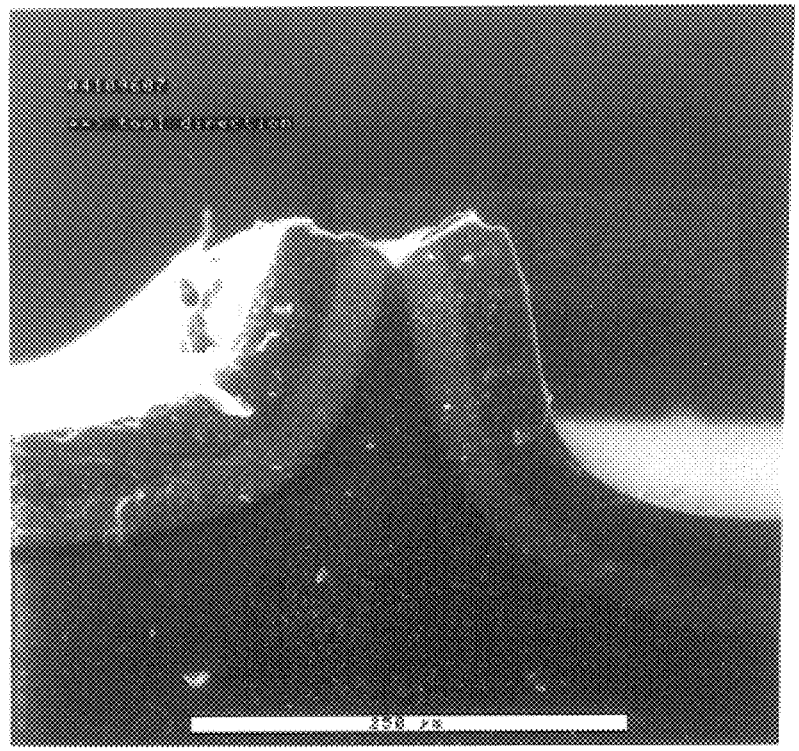
FIG. 22A is an ESEM micrograph at magnification 200× of a cross-sectional view of the Panel N of Mode II showing localized corrugation.
Figure 22B:
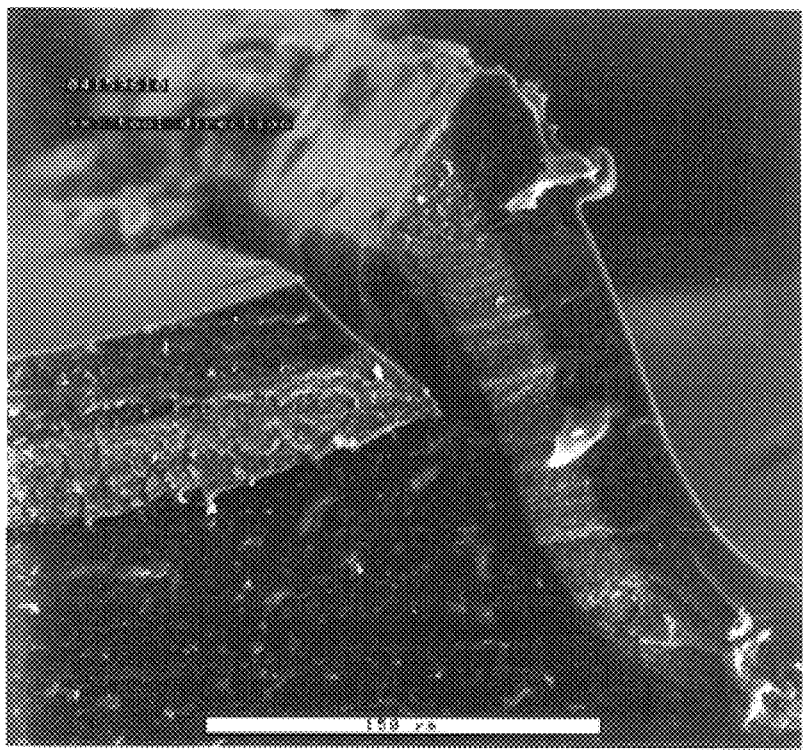
FIG. 22B is an ESEM micrograph at magnification 300× of a cross-sectional view of the Panel N of Mode II showing localized corrugation.

Mode II shows corrugated scuff damage with a periodically cut paint surface (FIG. 19). Mode II is very different from Mode I and mainly occurs in stiffer substrates 150. The localized corrugation is formed by severe plastic deformation of the paint layer or film 152 and a thin layer of substrate 150 (FIGS. 22A and 22B). The strong adhesion between paint layers or films 152 and substrate 150 was maintained even under the torturous deformation path. The onset failure mode of Mode II scuff damage was mostly adhesive in nature. This damage involves mainly friction induced, shorter wave length "stretch-fail" paint deformation and less substrate deformation. Thus, the parameters that control the scuff damage include friction, substrate stiffness and cohesive strength, adhesion between paint or film 152 and substrate 150, and strength of paint layers or film 152.

To use the system 100 for determining the scuff resistance of a film 152 on a substrate 150 and panel 154, the system 100 is placed in the initial, at rest position. In the initial at rest position, the actuator 36 of the testing module 10 is deactivated and the compression moving plate 14 is at its farthest point from the indentor support plate 12. Preferably, the indentor 24 or 224 is mounted on the indentor support plate 12. The exact shape, size and type of the indentor 24 or 224 would depend upon the panel 154 being tested and the type of test being performed. Next, the specimen or test panel 154 is mounted on the panel support plate 58. To mount the panel 154, the panel mounting rods 66 are first removed from the support plate 58. The panel 154 is then placed on the support plate 58 between the panel guide rods 68. The mounting rods 66 are then secured onto the panel support plate 58 over the top of the panel 154 such that the panel 154 is sandwiched between the panel support plate 58 and the panel mounting rods 66 and is securely held in place. Once the panel 154 is mounted, the panel support- plate 58 is secured to the bracket 60 and the panel 154 and the support plate 58 are then moved into the testing module 10 between the compression moving plate 14 and the indentor support plate 12. Preferably, in the initial, at rest position, the spacing between the compression moving plate 14 and the indentor support plate 12 is such that when the panel 154 and panel support plate 58 are moved between the compression moving plate 14 and the indentor support plate 12, the side of the panel support plate 58 opposite the panel 154 is adjacent to and in contact with the inner surface 14A of the compression moving plate 14 and the top portion 24B or alternately, the tip 224C of the indentor 24 or 224 is adjacent to and slightly spaced apart from the film 152 on the substrate 150 of the panel 154. To begin the testing, the computer 102 and the pressure control valves 104 are activated. The pressure or load supplied to the test module 10 is controlled by the pressure control valves 104. The rate at which the pressure (air) is supplied to the actuator 36 is controlled by the pressure rate needle control valve 106. As air is supplied to the actuator 36, the bellows 42 of the actuator 36 expand moving the compression moving plate 14 toward the indentor support plate 12. As the plate 12 is moved, the indentor 24 or 224 comes in contact with the film 152 on the substrate 150. Once the actuator 36 has reached the predetermined testing pressure, the indentation load, the bellows 42 stop expanding and hold the compression moving plate 14 stationary. The digital pressure indicator 118 will display the amount of pressure being supplied to the actuator 36. In the preferred embodiment, the bellows 42 are expanded almost instantaneously to their predetermined, testing position. Consequently, the initial contact between the indentor 24 or 224 and the panel 154 is sudden and at the full indentation load which causes the indentor 24 or 224 to compress or indent the film 152 and the substrate 150 of the panel 154. Once the actuator 36 is at the full indentation load, the panel support plate 58 with the panel 154 are moved down between the compression moving plate 14 and the indentor 24 or 224. The panel support plate 58 with the panel 154 may also be pulled or moved upward between the compression moving plate 14 and the indentor 24 or 224 depending on the initial position of the panel 154. The panel 154 and the panel support plate 58 are preferably moved at a slide speed of between 0.002 and 0.2 miles/hr. (50 and 5000 mm/min.). As the panel 154 is moved, the indentor 24 in contact with the film 152 on the substrate 150 causes a mar or scuff on the film 152 on the substrate 150. The amount of slide load exerted on the panel 154 is measured by the load cell 106 as a function of time and distance. The load cell 106 provides a signal to the computer 102 which plots the results on the plotter 108 as well as on the computer monitor. The computer 102 allows for precise control of the indentation load and the movement of the panel 154 which includes slide speed. In addition, as the panel 154 is moved or slid against the indentor 24 or 224, the indentation force can be varied to provide additional test results.

Figure 23:
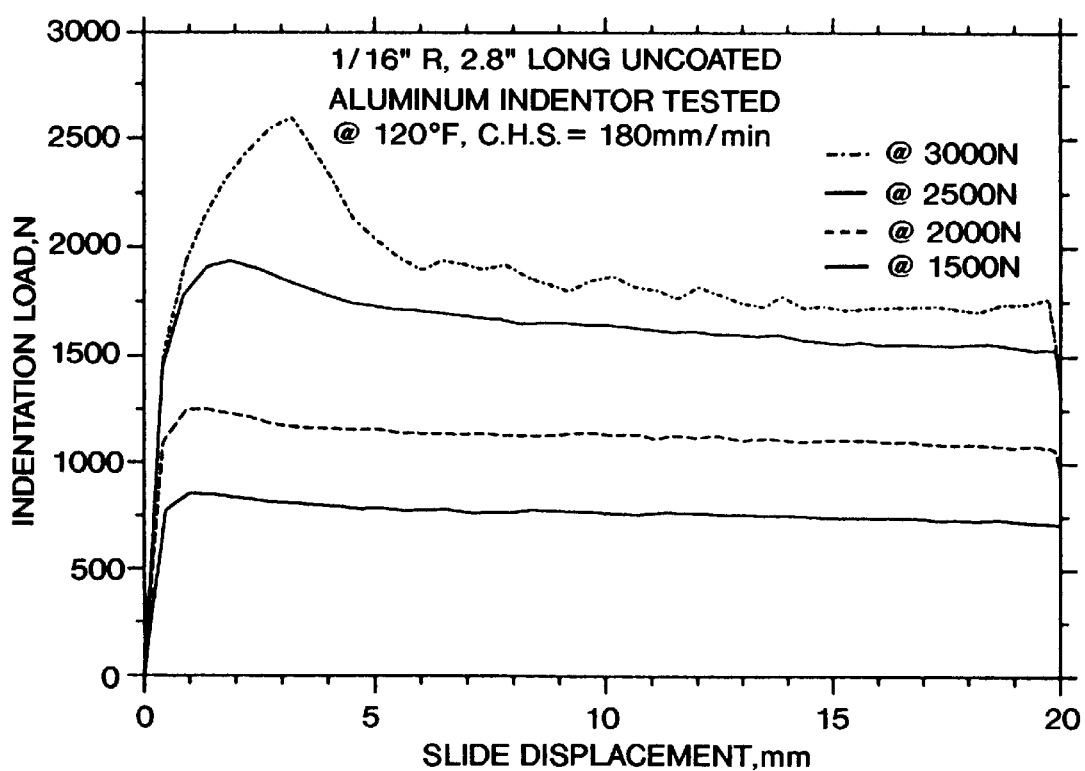
FIG. 23 is a plot showing typical Indentation-Slide Load versus Displacement for a coated TPO panel.

In the preferred embodiment, the computer 102 plots the indentation-slide load versus the slide displacement for each of the panels 154 tested (FIG. 23). The curves typically have an initial peak and a plateau region. The initial peak is mainly governed by the static friction of the indentor 24 or 224 against the film 152 and the cohesive strength of the substrate 150 of the panel 154. When the indentor 24 is sliding, the substrate 150 of the panel 154 is deformed at the edge of the initial indent formed during indentation loading. Similarly, the plateau load is determined by indentation load and dynamic friction between the surface of the indentor 24 or 224 and the film 152 which is partially controlled by the stiffness and strength of the substrate 150. In addition, the curves show that the correlation between the slide load and the indentation load is linear and the slope and the intercept of the curve at zero indentation load are closely related to the coefficient of friction between the surface of the indentor 24 or 224 and the film 152. The intercept was defined as an indentation-slide apparent friction and is used in some analysis.

The materials which were used to construct the substrates 150 of the test panels 154 included a range of thermoplastic polyolefins (TPO), polyurethanes (TPU), and reaction-injection molded PU (RIM-PU). The film 152 was constructed of various types of coating materials. In the preferred embodiment, one type of TPO panel, designated as TPO A, was chosen as a control system throughout the testing program. The other types of TPOs and other substrate systems which were tested in the system 100 were designated by alphabetical code systems. Detailed chemistry and processing information about the specific construction of the test panels 154 is not available because of the proprietary nature of those materials and processes. All TPO substrate panels 154 which were tested were 4.0 in×6.0 in×0.125 inch thick (10 cm×15 cm×0.318 cm thick) injection-molded panels coated by standard painting procedures. All test panels 154 were prepared and supplied from Montell USA Inc., in Lansing, Mich. In the testing in the preferred embodiment, the indentor geometry or size included indentors 224 having a length of 6.0 inches (15.2 cm), 5.0 inches (12.7 cm) and 3.0 inches (7.62 cm) with a tip 224C radius of 0.25 inches (0.64 cm), 0.125 inches (0.318 cm), 0.0625 inches (0.1588 cm) and 0.005 inches (0.0127 cm). In the preferred testing, the indentor material or tool surface was either a coated tool surface or an uncoated aluminum surface. The indentation load levels in the preferred testing were up to 6000N (N=KgM/S$^2$). Two sliding speeds of 0.0067 mile/hr. (180 mm/min.) and 0.2 mile/hr. (5000 mm/min.) were used in the testing. The testing was conducted at temperatures of −22° F. (−30° C.), 120° F. (48° C.) and 180° F. (82° C.) using a rigid support backing for the panel substrate 150. In the preferred embodiment, the testing was preformed at a temperature of 120° F. (48° C.) with a slide speed of 0.0067 miles/hr. (180 mm/min) as a function of indentation load.

Prior to using the present system 100, a simple manual fixture was successfully used to simulate and reproduce the real service environment induced paint damage, and to identify effects of various test variables involved in the simulation. The various test variables which were involved were the indentor geometry, indentor material or surface condition/friction, indentation load levels, sliding speed and test temperature. These variables controlled damage types and threshold conditions. The optimum test conditions and procedure for scuff damage evaluation were standardized to use the results of the manual fixture tests as a quality assurance test.

In the preferred embodiment, four to six indentation-sliding tests as a function of indentation load level with a predetermined test condition were performed per panel type or composition to determine scuff damage thresholds, damage growth curve and apparent friction term, etc. All quantitative analysis was based on scuff damage area. Damage modes were also characterized by an optical microscope or an electron scanning electron microscope.

EXAMPLE I

To correlate the observed critical failure mode to the complex stress states in the coating or film 152, interface and substrate region and, subsequently to formulate a damage prediction model in terms of material properties and test parameters, FEM stress and strain field analysis using ABAQUS® version 5.4-1 was conducted. Both linear elastic and non-linear elasto-plastic analysis were attempted with a model system consisting of only one 5 mils thick layer of coating material and substrate. The loading mode used was two step sequential loading to simulate actual dynamic contact. The output indicated that all of the normal stress fields showed a predicted distribution, i.e., it was highest at the contact point. However, the highest shear stress occurred at and under the interface. This was consistent with the ESEM observation.

EXAMPLE II

Figure 24:
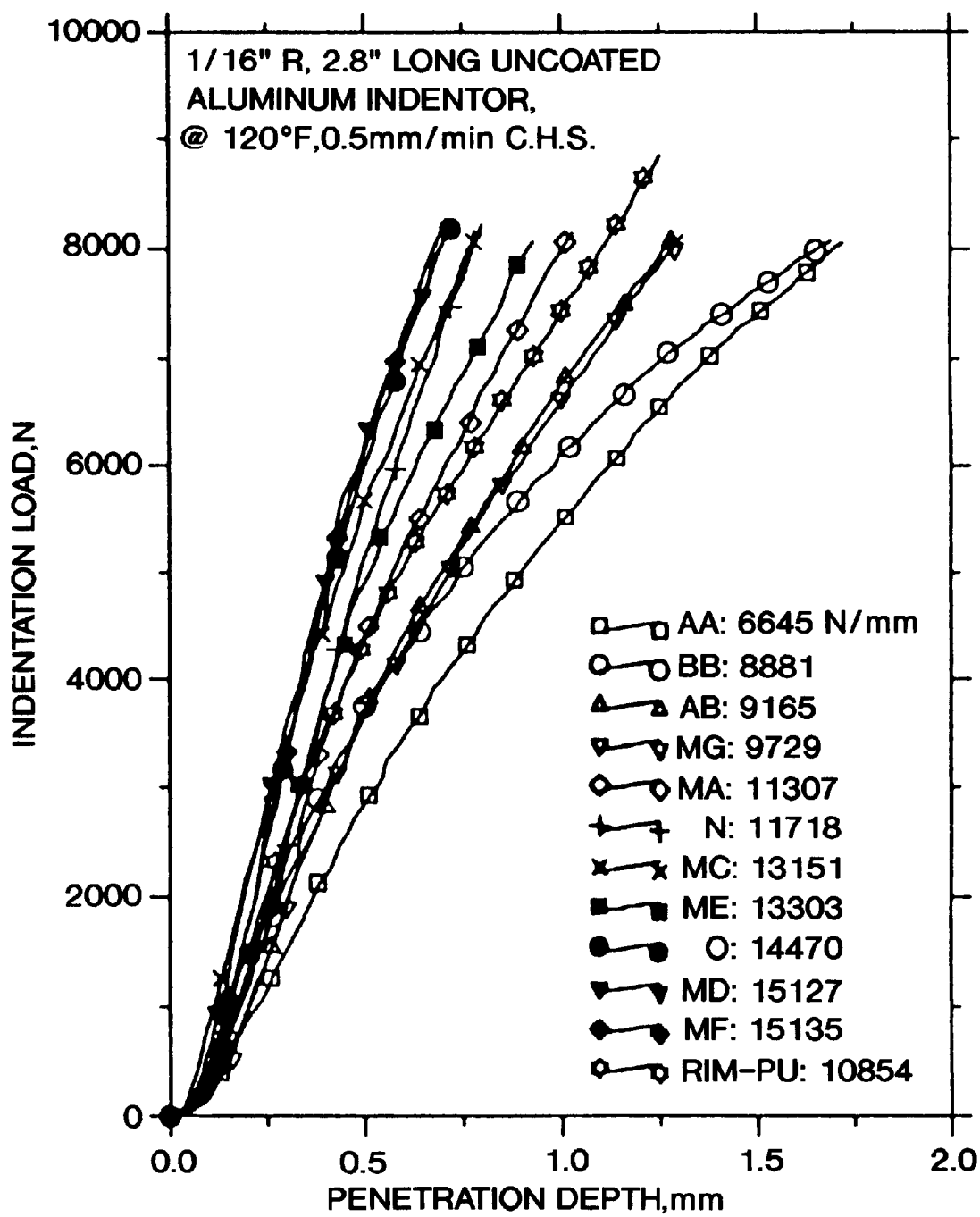
FIG. 24 is a plot of the indentation load versus the penetration depth for various TPO and RIM-PU panels using an indentor 24 constructed of uncoated aluminum having a length of 2.8 inches (7.1 cm) with a top portion radius of 0.0625 inch (0.1588 cm) conducted at a temperature of 120° F (49° C.) with a slide speed of 0.5 mm/min.
Figure 25:
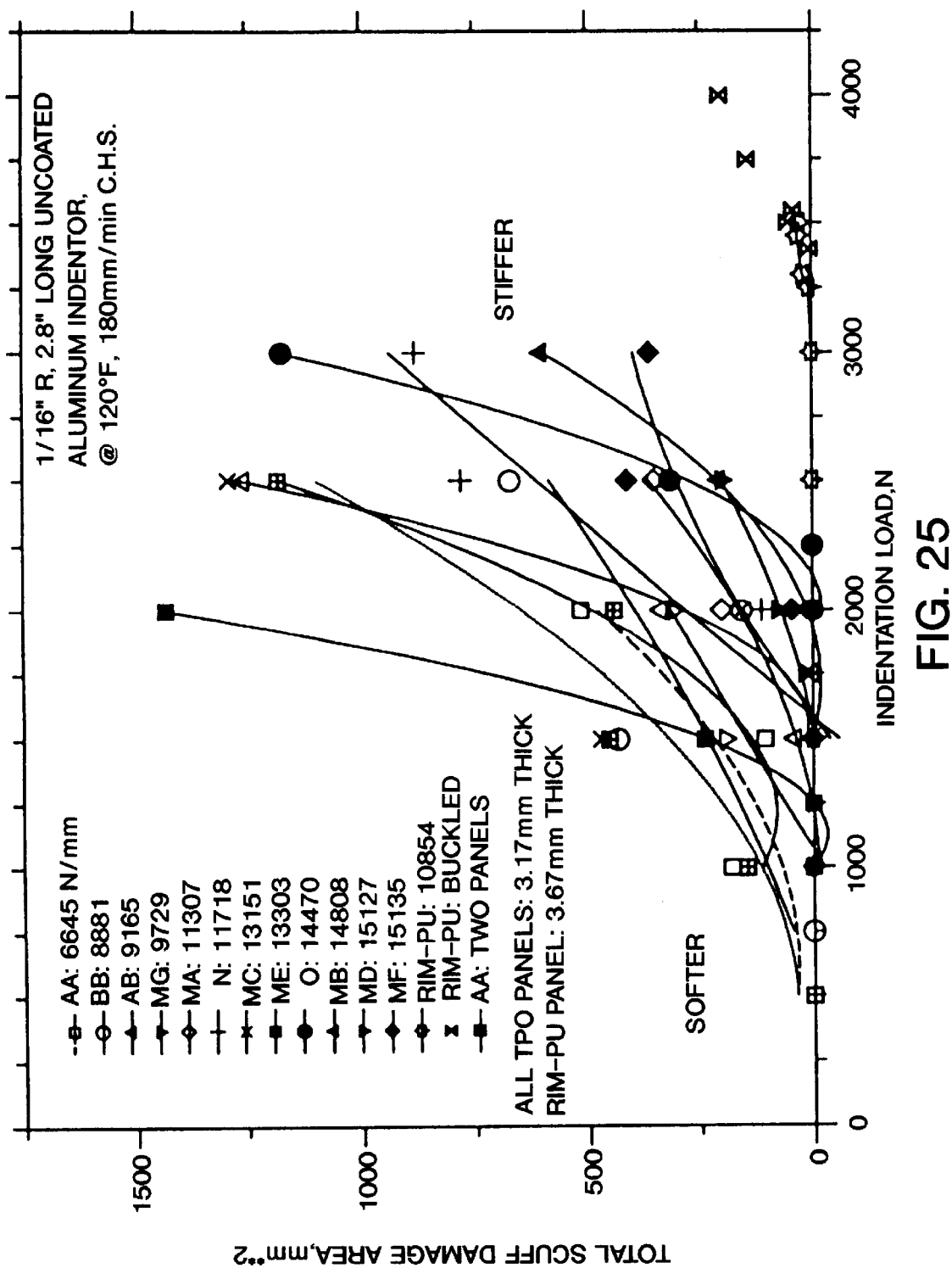
FIG. 25 is a plot showing the total scuff damage area versus the indentation load for various TPO and RIM-PU panels using an indentor 24 constructed of uncoated aluminum having a length of 2.8 inches (7.1 cm), with a top portion radius of 0.0625 inch (0.1588 cm) conducted at a temperature of 120° F. (49° C.) and a slide speed of 180 mm/min.
Figure 26:
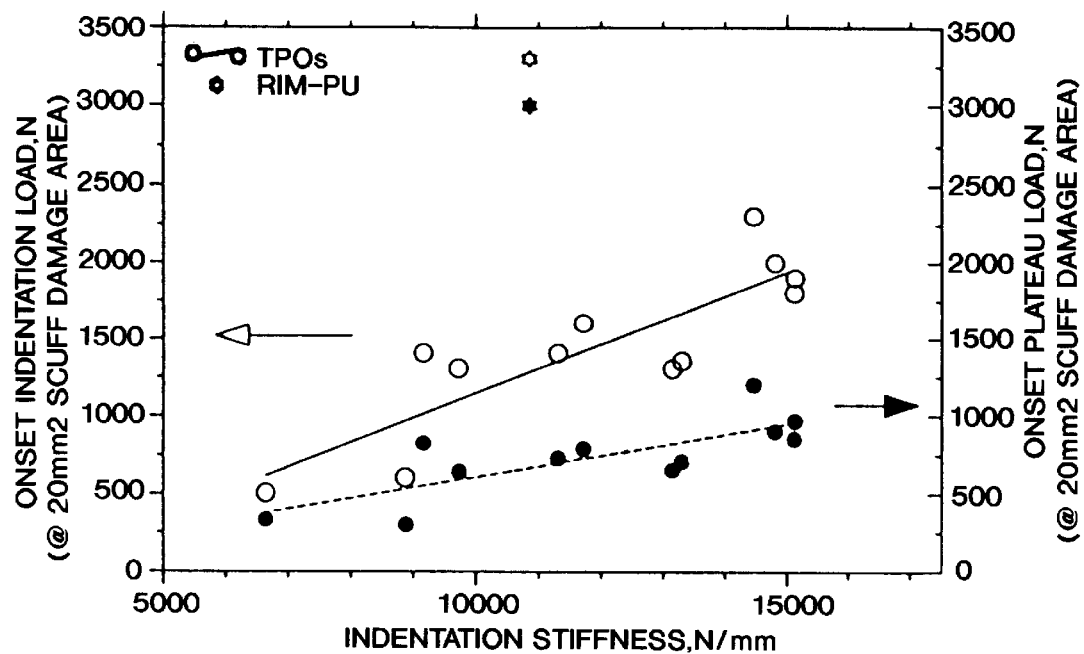
FIG. 26 is a plot on the onset indentation load versus indentation stiffness which shows the damage threshold as a function of substrate stiffness of TPO and RIM-PU panels.

A systematic Indention-slide testing system analysis was conducted as a function bf substrate composition. Twelve modified TPO substrates coated with one paint system and a RIM-PU with a similar paint system were studied. The various test panels had a range of substrate stiffness from 6,645 N/mm to 15,135 N/mm as determined from the indentation load versus penetration depth curve (FIG. 24). The Panel "AA" was identical to that of the control panel. The stiffness of the RIM-PU panel was about in the middle among those of the TPO panels. The indentation stiffness of both the TPO and the RIM-PU panels was measured based on the same panel thickness. The total scuff damage area after each indentation-sliding test was plotted against the indentation load for various panel systems (FIG. 25). In general, for the softer substrate, the scuff damage occurred at a lower indentation load with a moderate damage growth rate and then, with increasing stiffness up to the intermediate range, the onset load increased but the damage growth rate reached the maximum in exponential mode. With further increasing stiffness, the onset load increased but the damage growth rate decreased. This indicated a possible damage mode change with substrate stiffness and/or strength modification. In the case of the RIM-PU panel, the damage growth with increasing indentation load was at the lowest level compared to the TPO panels. In addition, the higher indentation loads, the RIM-PU panel failed before paint scuff damage, due to substrate buckling. The tests show that the damage threshold condition is directly related to substrate stiffness, i.e., higher onset load with increasing stiffness (FIG. 26). The onset indentation load was taken from the non-linear regression curves of total scuff damage area versus indentation load at a total scuff damage area of 20 mm (FIG. 25). The onset plateau load also increases with stiffness, though to a lesser extent (FIG. 26). The damage is controlled not only by friction, but also by substrate composition. The onset of damage in the RIM-PU panel was higher than that of the TPO panels despite the RIM-PU panels moderate stiffness. This suggests again that the damage is controlled by combination of various parameters, e.g., friction, substrate composition (stiffness), substrate cohesive strength and so on. However, the stiffer TPO panels, such as MB and MF, approached the performance of the RIM-PU panel (FIG. 25).

Figure 27:
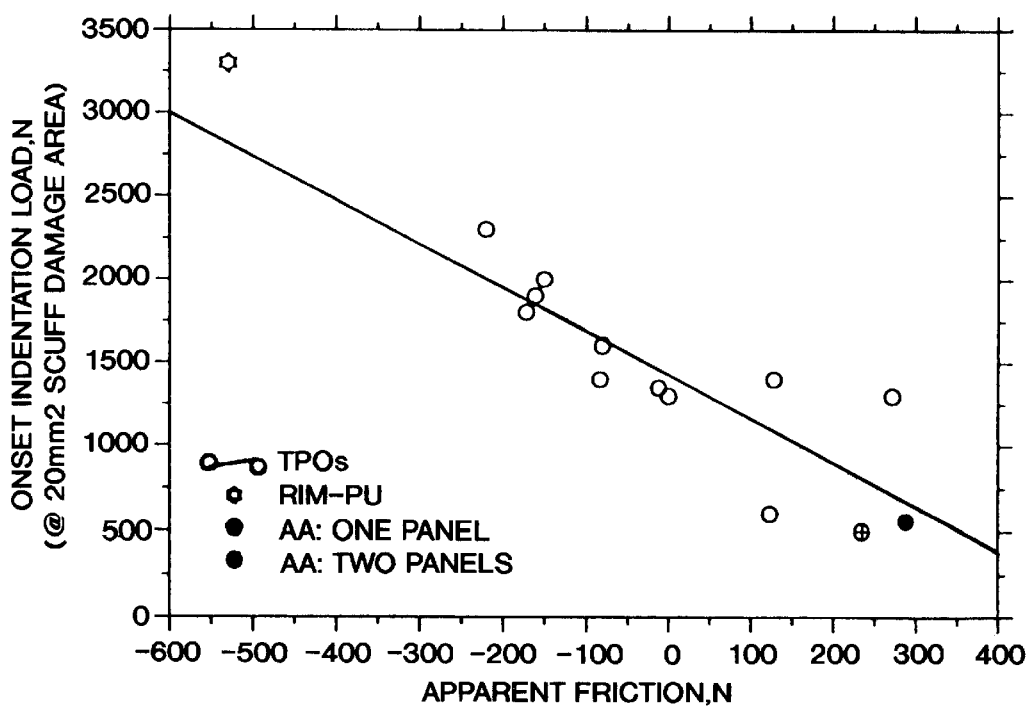
FIG. 27 is a plot of the onset indentation load or damage threshold versus apparent friction for TPO and RIM-PU panels.

It is believed that, the modification of substrate stiffness alters the friction characteristics of the paint surface or film 152. From regression analysis, comparing plateau slide load and applied indentation load, the apparent friction decreased monotonically with increasing substrate stiffness while the slope, the friction build-up rate, increased linearly with the stiffness. The apparent friction of the RIM-PU panel was the lowest but the friction build-up rate was the highest. Thus, the damage threshold was lowered with the increase of the apparent friction when the substrate stiffness was decreased (FIG. 27). Both the TPO and the RIM-PU panels showed a linear relationship. This indicates that the indentation-sliding apparent friction which represents not only a friction term but also a substrate composition term can be used as a measure of the coated panel performance.

Figure 28:
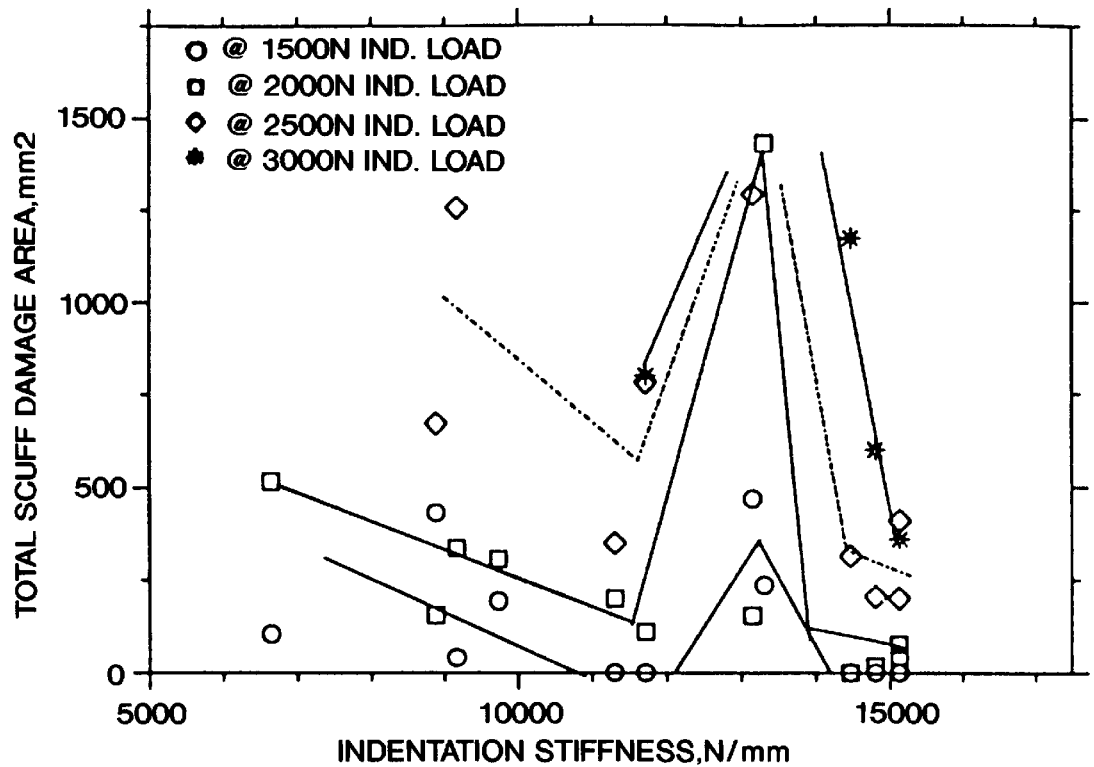
FIG. 28 is a plot of the total scuff damage area versus the indentation stiffness at various indentation loads for TPO panel systems.
Figure 29:
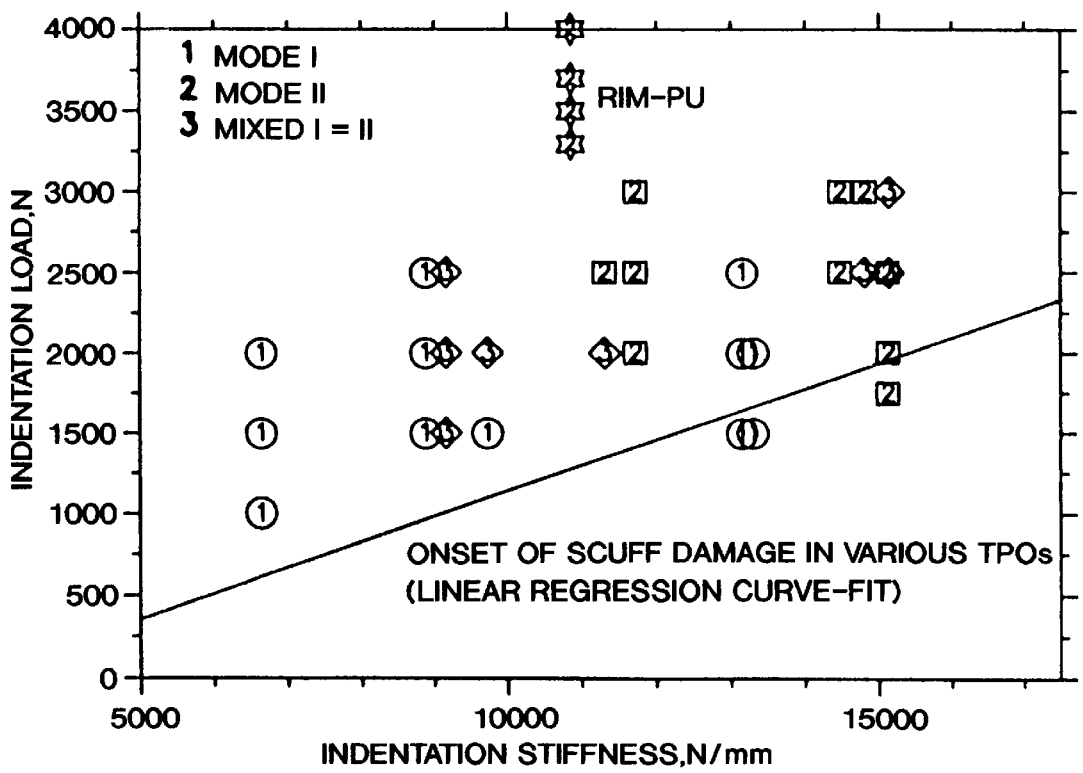
FIG. 29 is a plot of indentation load versus indentation stiffness which shows various damage modes for various TPO and RIM-PU panels.

The total scuff damage area was also plotted against indentation stiffness of the substrate at various indentation loads for the various panels (FIG. 28). Damage growth was not just linearly proportional to substrate stiffness but showed an abrupt peak at an indentation stiffness of about 13,000 N/mm at all indentation loads (FIG. 28). This bimodal behavior was explicitly manifested by the scuff damage mode change, i.e., from peeled off scuff (Mode I) to corrugated scuff (Mode II) (FIG. 29). Mode I occurred on the panels with lower stiffness and at the peak stiffness while the damage on the stiffer panels was generally Mode II. This unexpected behavior can be a genuine effect of the substrate composition, or it could be due to strength variation, morphological or microstructural changes in the substrates, or to any accidental changes in paint processing condition.

One concern in comparing scuff damage behavior of both TPO and RIM-PU panels was the thickness difference in test panels (FIG. 25). The indentor penetration depth is deeper in thicker substrates at a given indentation load and subsequently, the threshold conditions and growth of scuff damage can be altered with substrate thickness. To verify the effect of substrate thickness on scuff damage behavior, two identical TPO control Panels (AA) were stacked together for the indentation-slide scuff test. The overall scuff damage growth behavior of two panel system (crossed square symbols) was consistent with one panel system (open square symbol) and followed the trend in terms of substrate stiffness (FIG. 25). The threshold condition was almost identical in both cases (FIG. 27). This suggests that the damage is mainly controlled by applied indentation load, not by an amount of indentation deformation, i.e., substrate thickness does not control scuff damage behavior of painted panels.

EXAMPLE III

Figure 30:
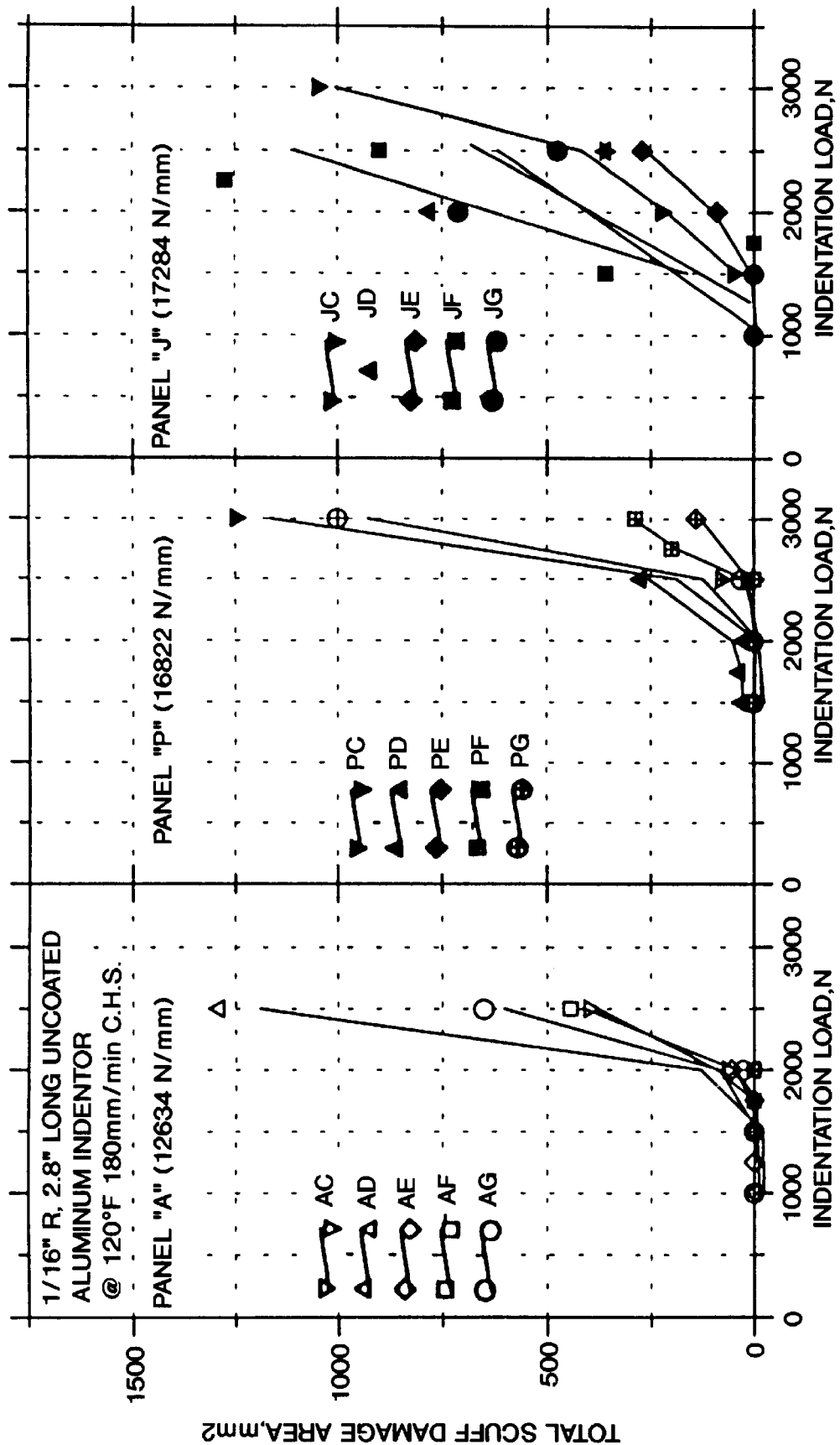
FIG. 30 is a plot of total scuff damage area versus indentation load for three (3) different TPO panels having five (5) different films (paint) 152.
Figure 31:
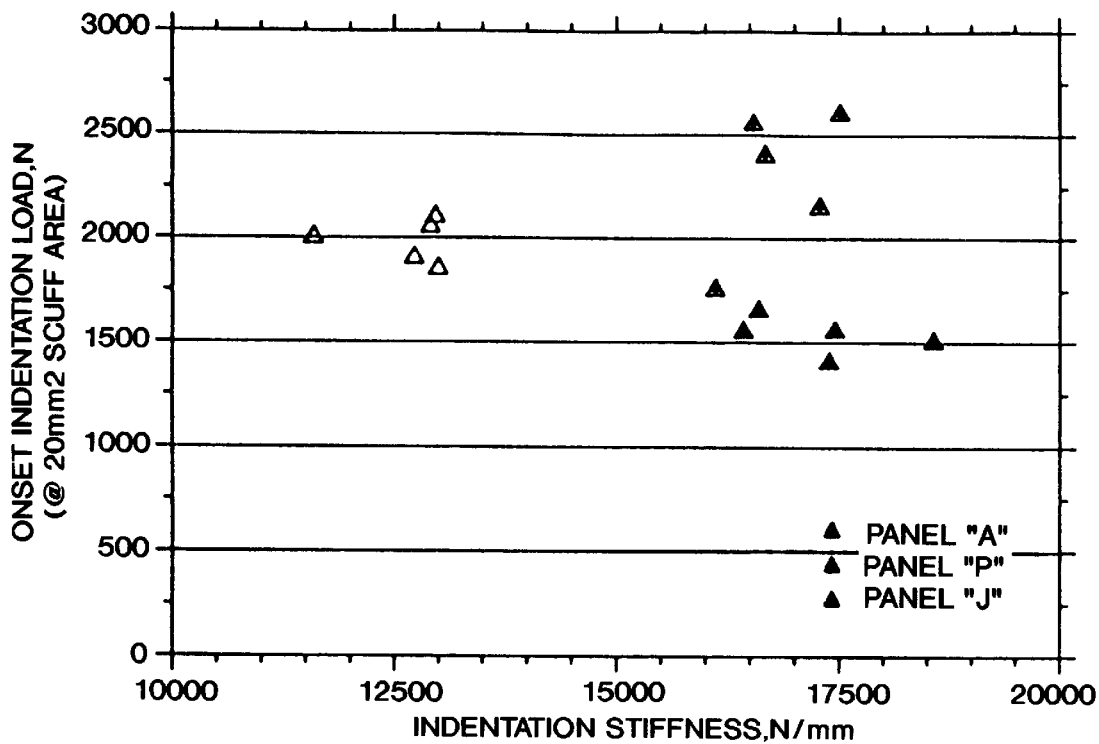
FIG. 31 is a plot of the onset indentation load versus the indentation stiffness for the three TPO panels of FIG. 30.
Figure 32:
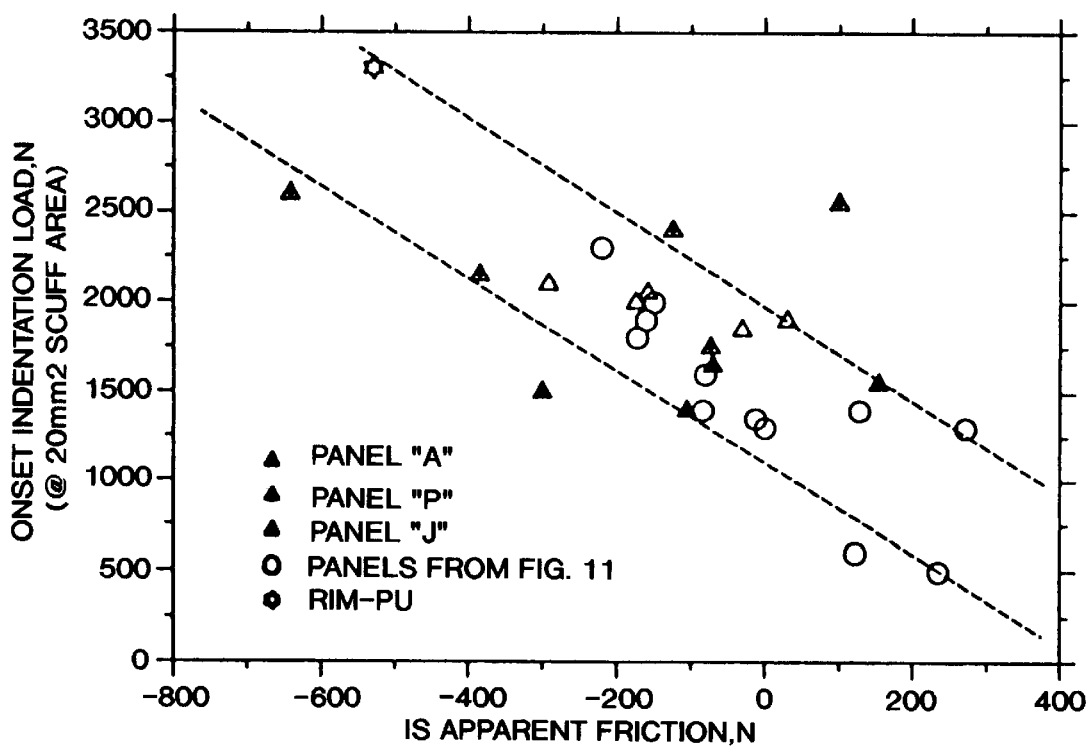
FIG. 32 is a plot of the onset indentation load versus the indentation-slide apparent friction for various TPO and RIM-PU test panels.

To further characterize critical parameters that control scuff damage of painted TPO panels, the combined effects of the paint system and the substrate type were investigated. Three composition types, designated as Panels "A", "P" and "J", coated with five different paint systems, designated as paint "C", "D", "E", "F" and "G", respectively, were characterized by the indentation-sliding scuff analysis. From the indentation load versus penetration depth curves, indentation stiffness of Panel "A" was about 12,600 N/mm while other Panels "P" and "J" was about 17,000 N/mm. The curves were almost independent of paint types. A plot of the overall results in terms of total scuff damage area as a function of indentation load showed a similar damage growth behavior except for some changes in threshold and rate depending on substrate or paint type (FIG. 30). Panel "P" exhibited the best performance in terms of scuff damage resistance. The results of a plot of the onset indentation load versus indentation stiffness clearly showed that the damage onset depends more on substrate composition and less on paint types in those systems studied (FIG. 31). The scuff onset load of Panel "J" was the lowest despite its high stiffness indicating complication of the controlling factors. If all the data in the onset load versus indentation-slide apparent friction plot is combined, (FIG. 32), it shows a general linear correlation within a bound, i.e., performance of painted plastic panels can be assessed by those terms. In addition, Panel "P" is closely approaching the performance of the RIM-PU panel.

EXAMPLE IV

Figure 33:
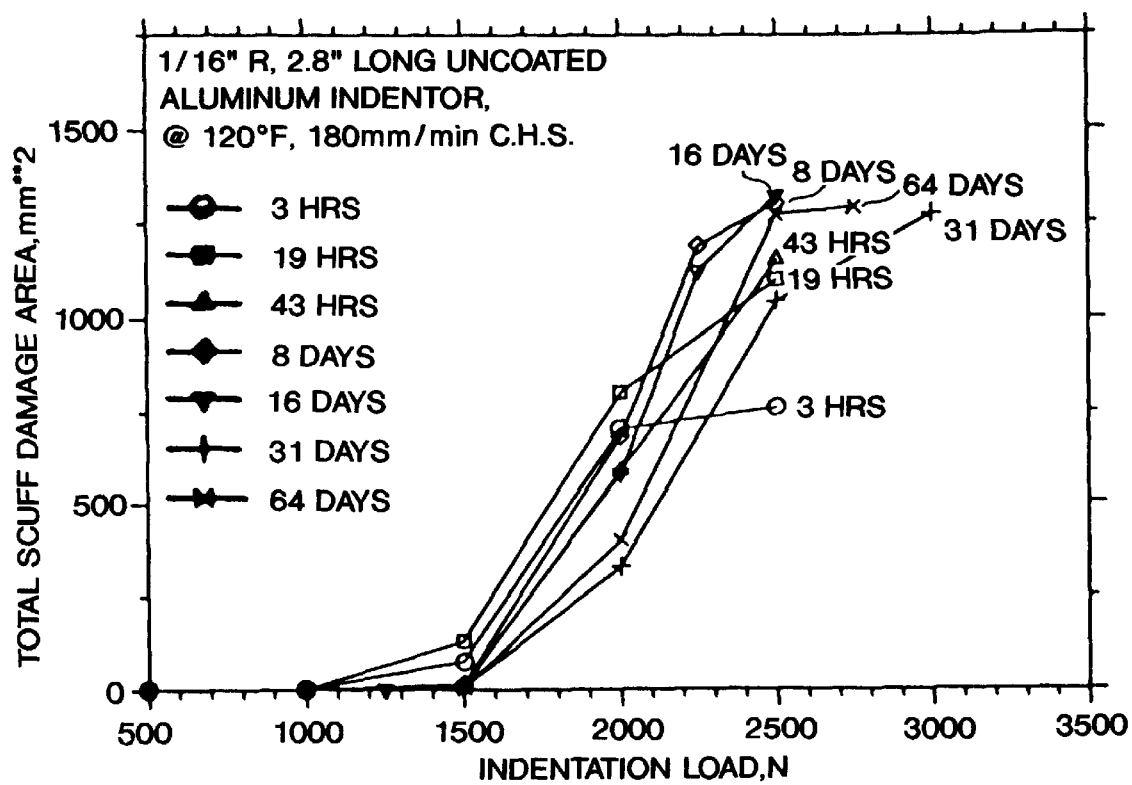
FIG. 33 is a plot of the total scuff damage area versus indentation load for TPO panel for different drying times.
Figure 34:
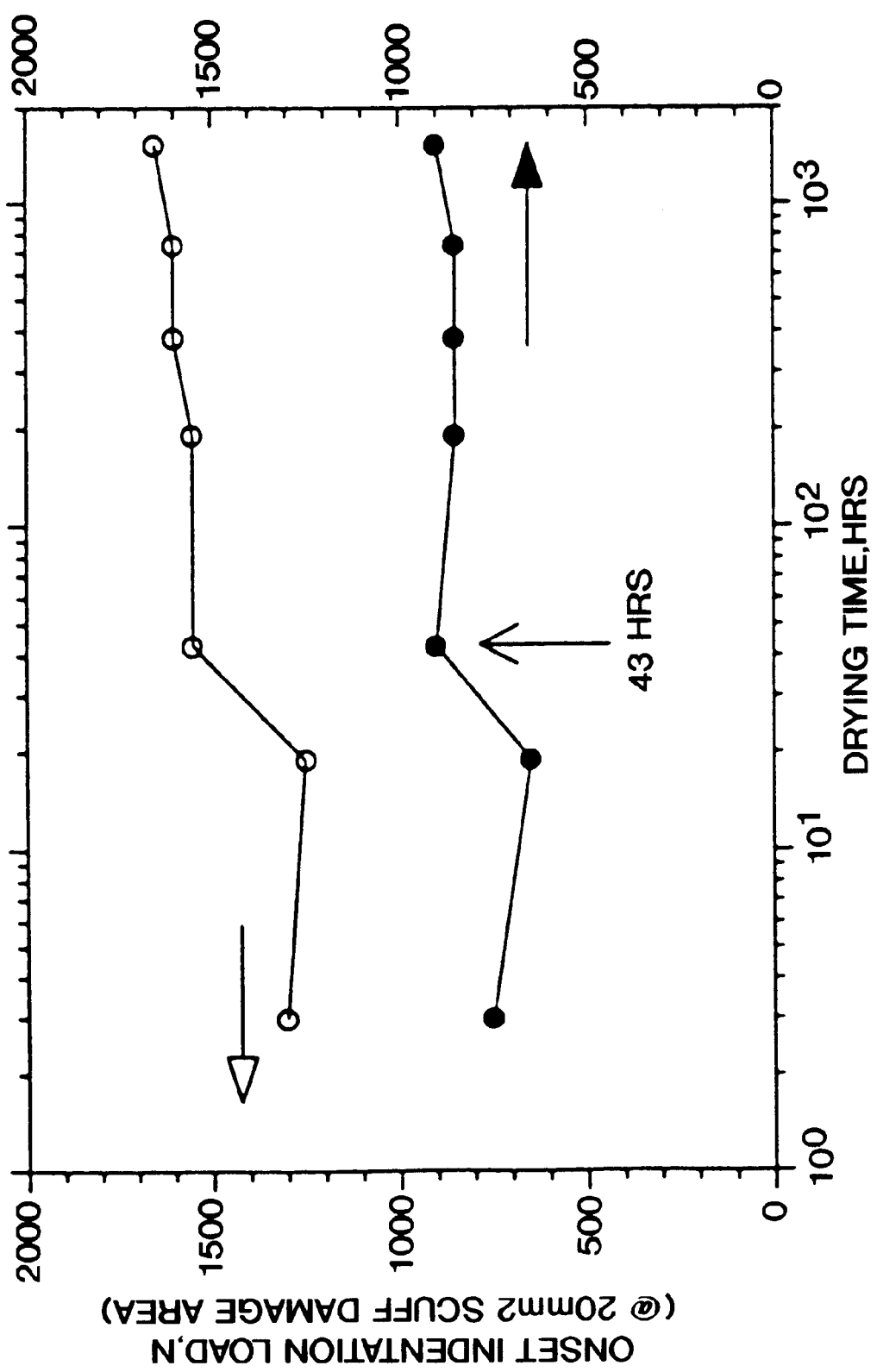
FIG. 34 is a plot of the onset indentation load or damage threshold versus the drying time for TPO panels.
Figure 35:
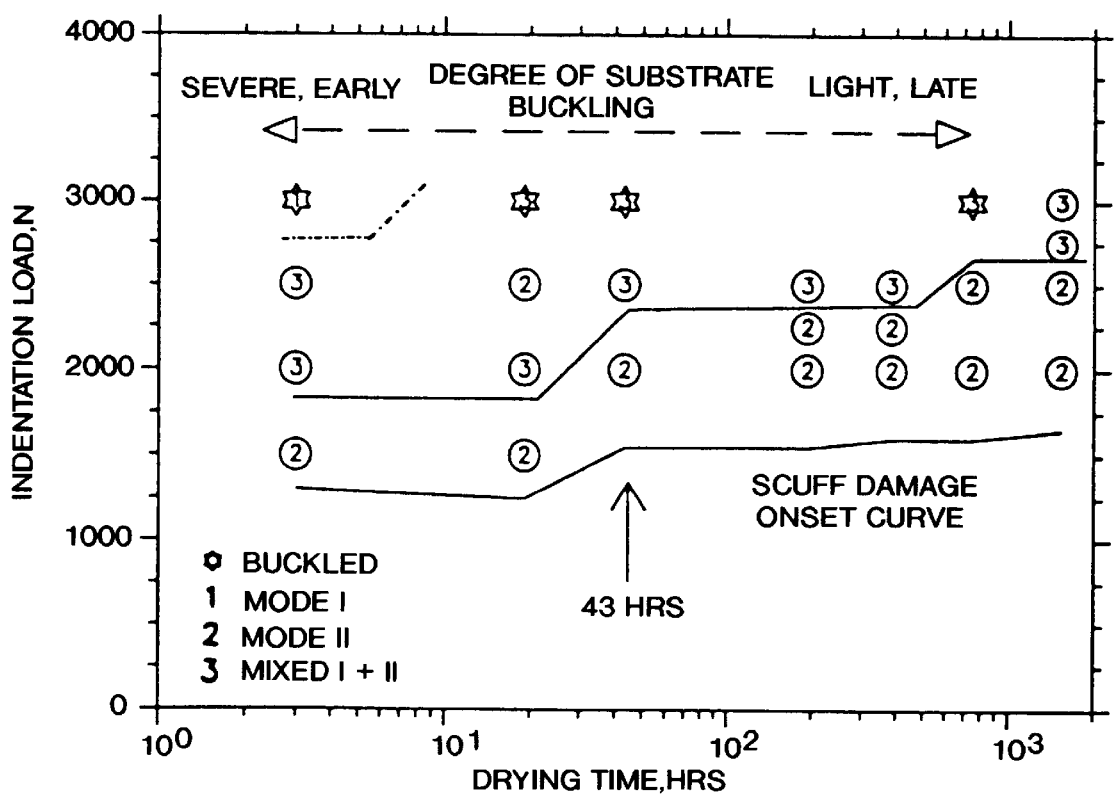
FIG. 35 is a plot of the indentation load versus the drying time for a TPO panel showing the damage modes.

Using a standardized indentation-sliding scuff test procedure with the optimum test variables, the effect of drying time of painted panels on scuff damage behavior was studied to investigate the effects of residual solvent trapped at the interface and/or substrate near the interface during painting process on the scuff damage performance as a function of drying time. The results can be used to optimize manufacturing fabrication processes in terms of storage time or assembly cycle in real automotive manufacturing line. Test panels made of a known TPO substrate and one paint type were prepared using a standard painting procedure. The panels were stored at room temperature and room humidity condition with the painted surface open to the air for drying. The indentation-sliding scuff analysis was then conducted as a function of drying time, such as, 3 hrs, 19 hrs, 43 hrs, 8 days, 16 days, 31 days and 64 days. The overall test results were plotted in terms of total scuff damage area versus indentation load as a function of drying time (FIG. 33). Comparing the results to the typical indentation-slide load displacement curves for a wide range of substrate compositions (FIG. 24), the damage growth curves of the present Example did not vary much in response to drying time except the for the very short drying times such as 3 hrs and 19 hrs. This change is clearly demonstrated from the onset indentation load-drying time curves (FIG. 34). At about 40 hrs drying, the onset load increased abruptly but then stayed at the almost same level for longer drying times. The painted panels are more susceptible to the contact induced scuff damage at the earlier drying times probably due to some residual solvent trapped in the film. This change does not seem to be controlled by friction because the onset slide (plateau) load-drying time curve also shows the same change. Otherwise, the onset load calculated from the plateau slide load (FIG. 23) which is the critical friction term for the damage should be constant regardless of drying time. This interpretation is further supported by the fact that the indentation-sliding apparent friction was almost constant through most of the drying times. The change of the substrate stiffness and/or strength by continuous drying is the most important factor (FIG. 35). At the higher indentation loads, most of panels showed some degree of substrate buckling except for at the longest drying time, 64 days. However, the intensity of buckling varied with drying time, i.e., severer at the shorter drying times and lighter with increasing drying time. The change is also clearly manifested by the damage mode changes from Mode II to mixed mode and then to Mode I. For the shorter drying times, the change occurred at the lower indentation loads but the transition load increased with drying time. Based on previous observation that the Mode I was mostly from softer substrates which are less resistant to damage while the Mode II was from stiffer and more resistant substrates and the buckling behavior, it can be concluded that the shift of the onset load results from the change of the substrate stiffness and strength with drying time.

A reliable testing module 10 and system 100 and reproducible testing procedure has been developed to assess the relative performance of painted plastic substrate panels 154 during dynamic contact-induced events. The system 100 simulates real service environment induced scuff damage and provides a useful tool to guide the development of more durable and robust painted plastic systems. The system 100 allows for successfully quantifying onset conditions and growth behavior of the scuff damage and demonstrates how to identify the most critical parameters that control the damage factors. The systematic indentation-sliding analysis reveals that the scuff damage resistance of the painted plastics is determined by combinations of various controlling parameters in a synergistic manner. However, in general, lowering the coefficient of friction on the paint surface or increasing stiffness and/or friction on the cohesive strength of substrate raises the threshold of the scuff damage. Thus, based on the same principles, the threshold is higher at lower temperatures or at the higher slide speeds. It is however, necessary to identify and quantify the effect of each individual parameter as well as their synergistic effects on various modes of dynamic contact induced paint damage for the ultimate in materials and process optimization.

It is intended that the foregoing description be only illustrative of the present invention and that the present invention be limited only by the hereinafter appended claims.

We claim:

1. A test module which mounts in an apparatus for determining resistance to scuff damage of a film adhered on a substrate which comprises:

(a) a frame for the module which mounts in the apparatus;

(b) spaced apart plates provided on the frame so that one of the spaced apart plates is movable towards and away from the other of the spaced apart plates on the frame and is guided by the frame during movement, each of the spaced apart plates having at least one face wherein the spaced apart plates are provided on the frame such that the face of one spaced apart plate is adjacent and parallel to the face of the other spaced apart plate and wherein the face of the one spaced apart plate remains parallel to the face of the other spaced apart plate during movement of one of the spaced apart plates;

(c) a slidable support plate positioned between the adjacent and parallel faces of the spaced apart plates for mounting the substrate and film between the adjacent and parallel faces of the spaced apart plates;

(d) an indentor with a rounded tip provided on the face of one of the spaced apart plates;

(e) an actuator means mounted on the frame and connected to one of the spaced apart plates to move one of the spaced apart plates towards the slidable support plate having the substrate and film and the other of the spaced apart plates with the other spaced apart plate remaining stationary such that the indentor is in contact with the film wherein the actuator means provides a preselected load per unit area by the indentor on the film and the indentor acts to scuff the film as the slidable support plate is moved while the indentor is in contact with the film; and (f) means connected to the slidable support plate for measuring a force applied for moving the slidable support plate between the faces of the spaced apart plates to thereby determine the scuff damage to the film adhered to the substrate by the indentor.

2. A testing apparatus for determining resistance to scuff damage of a film adherent on a substrate, which comprises:

(a) a test module apparatus which comprises:

(1) frame for the module;

(2) spaced apart plates provided on the frame so that one of the spaced apart plates is movable towards and away from the other of the spaced apart plates on the frame and is guided by the frame during movement, each of the spaced apart plates having at least one face wherein the spaced apart plates are provided on the frame such that the face of one spaced apart plate is adjacent and parallel to the face of the other spaced apart plate and wherein the face of the one spaced apart plate remains parallel to the face of the other spaced apart plate during movement of one of the spaced apart plates;

(3) a slidable support plate positioned between the adjacent and parallel faces of the spaced apart plates for mounting the substrate and film between the adjacent and parallel faces of the spaced apart plates;

(4) an indentor with a rounded tip provided on the face of one of the spaced apart plates; and (5) an actuator mounted on the frame and connected to one of the spaced apart plates to move one of the spaced apart plates towards the slidable support plate having the substrate and film and the other of the spaced apart plates with the other spaced apart plate remaining stationary such that the indentor is in contact with the film wherein movement of the actuator is provided by a fluid inside bellows in the actuator which provides a preselected load per unit area by the indentor on the film and the indentor acts to scuff the film as the slidable support plate is moved while the indentor is in contact with the film;

(b) a load cell connected by a bracket to the slidable support plate;

(c) gauge means for determining the load per unit area applied by the indentor on the film; and (d) supply means for introducing the fluid into the bellows of the actuator.

3. A test module which mounts on an apparatus for determining resistance to scuff damage of a film adhered on a substrate which comprises:

(a) an indentor with a rounded tip on a first side positionable against the film on the substrate;

(b) an indentor support plate with a planar face which mounts the indentor on a second side of the indentor opposite the first side with the tip;

(c) parallel rods mounted on the indentor support plate perpendicular to the planar face;

(d) a movable plate mounted on the rods so as to be movable towards and away from the indentor support plate with a planar face parallel to the planar face of the indentor support plate and perpendicular to the rods, wherein the substrate is movable in a space between the movable plate and the indentor support plate with the indentor against the film;

(e) an end plate secured on the rods spaced from the space between the movable plate and indentor support plate which holds the rods in position for movement of the movable plate;

(f) a slidable support plate positioned between the indentor support plate and the movable plate for mounting the substrate and the film between the indentor support plate and the movable plate;

(g) an actuator mounted between the end plate and the movable plate, wherein movement of the actuator is produced by providing a fluid inside an expandable bellows in the actuator which moves the movable plate towards the slidable support plate and the indentor support plate such that the indentor is in contact with the film as the bellows expand to produce a preselected load per unit area of the indentor against the film; and (h) means connected to the slidable support plate for measuring a force applied for moving the slidable support plate between the faces of the spaced apart plates to thereby determine the scuff damage to the film adhered to the substrate by the indentor.

4. The apparatus of claim 3 wherein the fluid is air.

5. The apparatus of any one of claims 3 or 4 wherein the indentor has an elongated rounded tip.

6. The apparatus of claim 3 wherein the movable plate has bearings which engage the rods.

7. The apparatus of claim 3 wherein the movable plate has multiple parallel grooves so as to reduce friction between the slidable support plate and the movable plate.

8. The apparatus of claim 3 wherein the movable, indentor support and end plates are rectangular with four corners and the rods are mounted at each of the corners of the end plate and the indentor support plate.

9. The apparatus of claim 3 wherein the rods have a circular-cross section.

10. A testing apparatus for determining resistance to scuff damage of a film adhered on a substrate which comprises:

(a) a test module which comprises:

(1) an indentor with a rounded tip on a first side positionable against the film on the substrate;

(2) an indentor support plate with a planar face which mounts the indentor on a second side of the indentor opposite the first side with the tip;

(3) parallel rods mounted on the indentor support plate perpendicular to the planar face;

(4) a movable plate mounted on the rods so as to be movable towards and away from the indentor support plate with a planar face parallel and adjacent to the planar face of the support plate and perpendicular to the rods, wherein in use the substrate is moved in a space between the movable plate and the indentor support plate with the indentor against the film;

(5) an end plate secured on the rods spaced from the space between the movable plate and indentor support plate which holds the rods in position for movement of the moveable plate;

(6) a slidable support plate positioned between the planar face of the indentor support plate and the planar face of the movable plate for mounting the substrate and film between the adjacent and parallel planar faces of the indentor support plate and the movable plate;

(7) an actuator mounted between the end plate and the movable plate, wherein movement of the actuator is produced by providing a fluid inside bellows in the actuator which moves the movable plate towards the indentor to produce preselected load per unit area of the indentor against the film;

(b) a load cell connected by a bracket to the slidable support plate;

(c) gauge means for determining the load per unit area applied by the indentor support plate with the indentor on the film; and (d) supply means for introducing the fluid into the bellows of the actuator at a pressure which provides the load per unit area.

11. The apparatus of claim 10 wherein the movable plate, the indentor support plate and the end plate are rectangular with four corners and wherein the rods are mounted at each of the corners of the end plate and the indentor support plate.

12. The apparatus of claim 10 wherein the rods have a circular cross-section.

13. The apparatus of claim 10 wherein the fluid is air.

14. The apparatus of claim 10 wherein the movable plate has grooves so as to reduce friction.

15. A method of testing for resistance to scuffing of a film adhered on a substrate which comprises:

(a) providing a testing apparatus for determining resistance to scuff damage of the film adhered on the substrate which comprises: a test module apparatus which comprises a frame for the module which mounts in the apparatus; spaced apart plates provided on the frame so that one of the spaced apart plates is movable towards and away from an other of the spaced apart plates on the frame and is guided by the frame during movement, each of the spaced apart plates having at least one face wherein the spaced apart plates are provided on the frame such that the face of one spaced apart plate is adjacent and parallel to the face of the other spaced apart plate and wherein the face of the one spaced apart plate remains parallel to the face of the other spaced apart plate during movement of one of the spaced apart plates; a slidable support plate positioned between the adjacent and parallel faces of the spaced apart plates for mounting the substrate and film between the adjacent and parallel faces of the spaced apart plates; an indentor with a rounded tip provided on the face of one of the spaced apart plates; and actuator means mounted on the frame and connected to one of the spaced apart plates to move one of the spaced apart plates towards the slidable support plate having the substrate and film and the other of the spaced apart plates with the other spaced apart plate remaining stationary such that the indentor is in contact with the film, wherein the actuator means provides a preselected load per unit area by the indentor on the film and the indentor acts to scuff the film as the slidable support plate is moved while the indentor is in contact with the film;

means connected to the slidable support plate for measuring a force applied for moving the slidable support plate in the test module apparatus between the spaced apart plates with the indentor against the film; and gauge means for determining the load per unit area applied by the indentor against the film;

(b) engaging the indentor against the film;

(c) moving the substrate between the spaced apart plates with the indentor against the film on the substrate; and (d) determining the scuff resistance of the film on the substrate as a function of the load per unit area applied on the film by the indentor.

16. The method of claim 15 wherein movement of the actuator means is provided by a fluid inside a bellows.

17. The method of claim 16 wherein a supply means is provided for introducing the fluid into the bellows of the actuator means.

18. The method of claim 16 wherein the load per unit area provided by the actuator means as a result of the fluid inside the bellows is constant as a function of time as the substrate and film are moved.

19. The method of claim 16 wherein the load per unit area provided by the actuator means as a result of the fluid inside the bellows is variable as a function of time as the substrate and film are moved.

20. A test module which mounts on an apparatus for determining resistance to scuff damage of a film adhered on a substrate which comprises:

(a) an indentor with a rounded tip on a first side positionable against the film on the substrate;

(b) an indentor support plate with a planar face which mounts the indentor on a second side of the indentor opposite the first side with the tip;

(c) parallel rods mounted on the indentor support plate perpendicular to the planar face;

(d) a movable plate mounted on the rods so as to be movable towards and away from the indentor support plate with a planar face parallel and adjacent to the planar face of the support plate and perpendicular to the rods, wherein the substrate is moved in a space between the movable plate and the indentor support plate with the indentor against the film;

(e) an end plate secured on the rods spaced from the space between the movable plate and indentor support plate which holds the rods in position for movement of the movable plate;

(f) a slidable support plate positioned between the planar face of the indentor support plate and the planar face of the movable plate for mounting the substrate and film between the adjacent and parallel faces of the indentor support plate and the movable plate;

(g) an actuator mounted between the end plate and the movable plate, wherein movement of the actuator is produced by providing a fluid inside an expandable bellows in the actuator which moves the movable plate towards the indentor as the bellows expands to produce a preselected load per unit area of the indentor against the film; and (h) means connected to the slidable support plate for measuring a force applied for moving the slidable support plate between the faces of the spaced apart plates to thereby determine the scuff damage to the film adhered to the substrate by the indentor.

* * * * *